(12) United States Patent
Marks

(10) Patent No.: US 6,208,941 B1
(45) Date of Patent: Mar. 27, 2001

(54) METHOD AND APPARATUS FOR ANALYSIS OF CHROMATOGRAPHIC MIGRATION PATTERNS

(75) Inventor: Andrew F. Marks, Sandy, UT (US)

(73) Assignee: University of Utah Research Foundation

( * ) Notice: Subject to any disclaimer, the term of this patent is extended or adjusted under 35 U.S.C. 154(b) by 0 days.

(21) Appl. No.: 08/933,211

(22) Filed: Sep. 16, 1997

Related U.S. Application Data

(60) Provisional application No. 60/025,241, filed on Sep. 16, 1996.

(51) Int. Cl.[7] .............................. C12Q 1/70; G01N 15/06
(52) U.S. Cl. ................................ 702/20; 382/129; 435/5; 435/9; 436/161; 436/163
(58) Field of Search .................................. 702/28, 19, 20; 382/129; 435/5, 6; 436/161, 163

(56) References Cited

U.S. PATENT DOCUMENTS

| | | | |
|---|---|---|---|
| 4,837,687 | 6/1989 | Tanaka et al. ................... | 364/413.01 |
| 4,868,749 | 9/1989 | Kimura et al. ................... | 364/413.13 |
| 4,885,696 | 12/1989 | Hara ..................................... | 364/497 |
| 4,888,695 | 12/1989 | Shiraishi et al. ................. | 364/413.13 |
| 4,894,786 | 1/1990 | Hara ..................................... | 364/497 |
| 4,939,667 | 7/1990 | Hara et al. ............................ | 364/497 |
| 4,941,092 | 7/1990 | Hara et al. ....................... | 364/413.15 |
| 4,958,281 | 9/1990 | Hara .................................. | 364/413.01 |
| 4,972,325 | 11/1990 | Hara ..................................... | 364/497 |
| 4,980,827 | 12/1990 | Hara ................................ | 364/413.01 |

(List continued on next page.)

FOREIGN PATENT DOCUMENTS

WO 9605565    2/1996   (WO) .

OTHER PUBLICATIONS

Toward Fully Automated Genotyping—Am.J.Human Genetics—p. 1199–1210 1995.
Toward Fully Automated Genotyping—Am.J.Human Genetics—p. 777–787 1994.
Fuzzy Logic to Improve 1st Pass Sequence and Establish Cutoffs and a Confidence Metric During Base Calling. Electronic Poster Abstract, Hilton Head Conference, 1995.
Utah Sequencing System: Sequencing and Assembly Module. Electronic Poster Abstract, Hilton Head Conference, 1994.
European Search Report.
Tsumoto, S. et al., "Automated Discovery of Functional Components of Proteins from Amino–acid Sequences based on Rough Sets and Change of Representation." First International Conference on Knowledge Discovery and Data Mining. Proceedings of First International Conference on Knowledge Discovery and Data Mining (KDD–95), Montreal, Que., Canada, Aug. 20–21, 1995, pp. 318–324.

(List continued on next page.)

*Primary Examiner*—Kamini Shah
(74) *Attorney, Agent, or Firm*—Parons Behle & Latimer

(57) ABSTRACT

The present invention includes a method and apparatus for the detection and analysis of information-containing signals in chromatographic data using iterative blind deconvolution and fuzzy logic algorithms. The invented method analyzes chromatographic data from a wide variety of sources of DNA sequencing information, including gel and capillary electrophoresis. Autoradiograms, single-fluor, four-lane and four fluor, single lane fluorescent chromatographic data are suitable sources of unprocessed input data. The output from the invented base calling method includes called (identified) sequence data and quality values for the called bases.

19 Claims, 26 Drawing Sheets

Microfiche Appendix Included
(5 Microfiche, 229 Pages)

U.S. PATENT DOCUMENTS

| | | | |
|---|---|---|---|
| 4,982,326 | | 1/1991 | Kaneko ............................. 364/413.01 |
| 5,098,536 | | 3/1992 | Anderson ........................... 204/180.1 |
| 5,119,316 | | 6/1992 | Dam et al. ............................ 364/498 |
| 5,218,529 | | 6/1993 | Meyer et al. .................... 364/413.01 |
| 5,273,632 | * | 12/1993 | Stockham et al. ................. 204/180.1 |
| 5,365,455 | * | 11/1994 | Tibbetts et al. ....................... 364/497 |
| 5,379,420 | | 1/1995 | Ullner .................................. 395/600 |
| 5,400,249 | | 3/1995 | Soll et al. ......................... 364/413.13 |
| 5,419,825 | | 5/1995 | Fujii ................................. 204/299 R |
| 5,443,791 | | 8/1995 | Cathcart et al. ........................ 422/65 |
| 5,488,567 | | 1/1996 | Allen et al. ........................... 364/497 |
| 5,502,773 | * | 3/1996 | Tibbetts et al. ....................... 382/129 |
| 5,541,067 | | 7/1996 | Perlin ........................................ 435/6 |
| 5,580,728 | | 12/1996 | Perlin ........................................ 435/6 |
| 5,604,100 | | 2/1997 | Perlin ........................................ 435/6 |
| 5,622,823 | | 4/1997 | Perlin ........................................ 435/6 |
| 5,741,462 | * | 4/1998 | Nova et al. ........................... 422/68.1 |
| 5,867,402 | * | 2/1999 | Scheider et al. ...................... 364/496 |
| 5,888,819 | * | 3/1999 | Goelet et al. ............................. 435/5 |

OTHER PUBLICATIONS

Kolaskar A. S. et al., "Parallel Computers in Biological Data Bank Management." New Data Challenges in our Information Age. Proceedings of the Thirteenth International CODATA Conference (in collaboration with the ICSU Panel on World Data Centers). Proceedings of the $13^{th}$ International CODATA Conference on New Data Challenges, pp. C/165–173, XP002119590, 1994 Paris, France, CODATA, France.

* cited by examiner

BadSpacing

Cross Banding

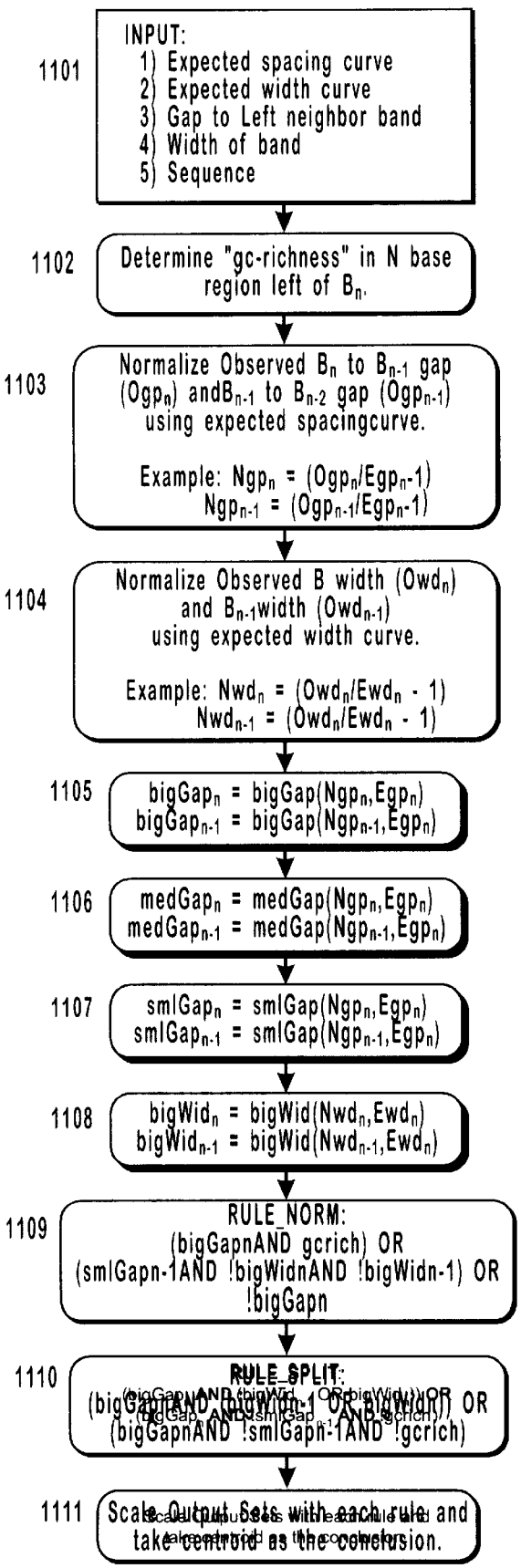
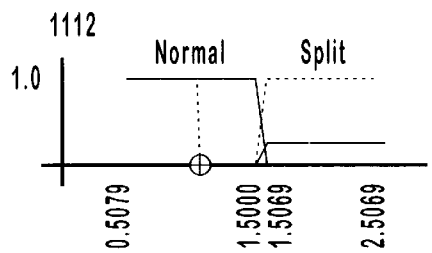
FIG. 11A
FIG. 11

BigWidth

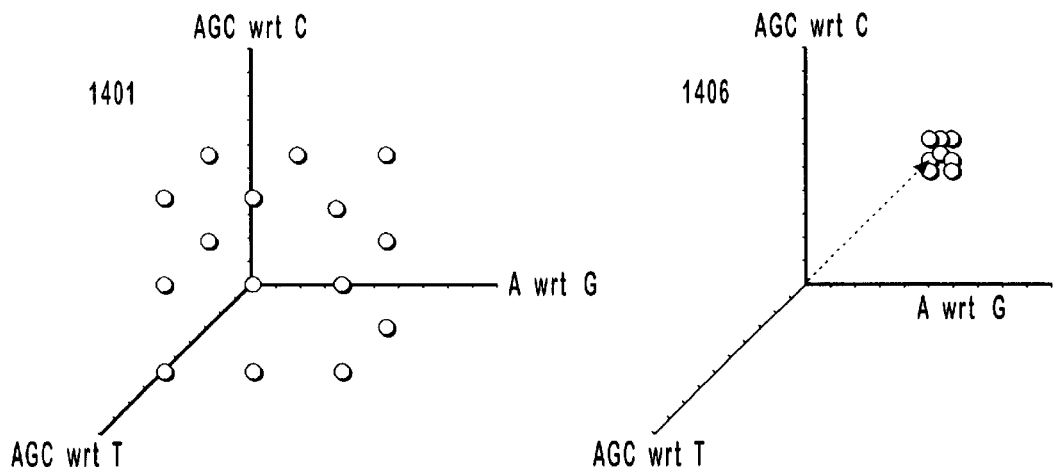
FIG. 14           FIG. 14C
Low Integral Alignment
High Integral Alignment
FIG. 14A           FIG. 14D
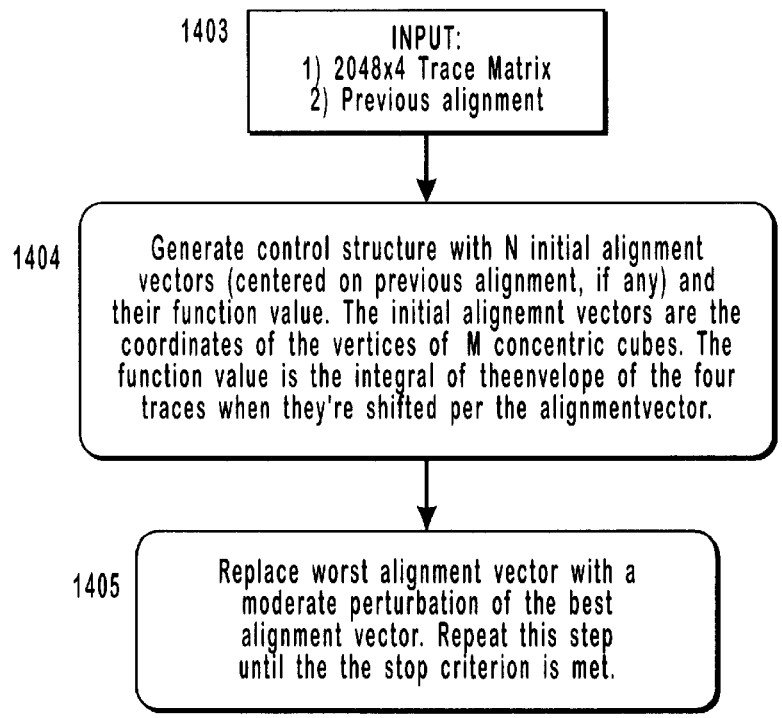
FIG. 14B Band Height Good Shape BQ OK Baseline Buzz BQ OK Spacing

2205

Forward, Backward, and Combined.

2206

Baseline subtracted

METHOD AND APPARATUS FOR ANALYSIS OF CHROMATOGRAPHIC MIGRATION PATTERNS

CONTINUITY

This patent application is a continuation-in-part of U.S. Provisional patent application Ser. No. 60/025,241, filed Sep. 16, 1996. The U.S. Government has a paid-up license in this invention and the right in limited circumstances to require the patent owner to license others on reasonable terms as provided for by the terms of Grant No. DEFG0394ER61950 awarded by the Department of Energy and Grant No. 5P50HG0019906 awarded by the National Institutes of Health.

REFERENCE TO MICROFICHE APPENDIX

A microfiche appendix, containing 5 microfiche and 229 total frames is filed herewith.

BACKGROUND OF THE INVENTION

A. Field of the Invention

This invention relates to the field of signal detection and analysis of chromatographic migration patterns as commonly applied to mixtures of molecules. More specifically, this invention relates to a method and apparatus for signal detection and analysis of chromatographic migration patterns as applied to the determination of DNA sequences.

B. Description of Related Art

The ability to efficiently and accurately detect and analyze information-containing signals in chromatographic data is important for handling large amounts of data. Such an ability is particularly important for projects such as the Human Genome Project, where large amounts of information will be generated which must be analyzed and integrated to produce a representative sequence of an entire human genome. To expedite the analysis of DNA sequence information, numerous methods have been developed. For example, a U.S. patent to Clark Tibbetts (U.S. Pat. No. 5,365,455) discloses a method for the automated processing of DNA sequence data. This patent is incorporated by reference herein in its entirety. The Tibbetts' method derives information from informative variables obtained from the input data set. Such informative variables may include the relative intensities between adjacent signals, the relative signal spacing and pattern recognition factors.

The Tibbetts' method is limited, however, by the quality of the chromatographic data. Tibbetts' method relies to a certain extent on the reproducibility of chromatographic data to train the base identification ("calling") system. The apparatus generating the chromatographic data, therefore, needs to be consistent from run to run to avoid retraining the algorithm. Because chromatographic data frequently contain background noise and migration aberrations which obscure information-containing signals, analyses based on signal spacing may produce errors in signal identification. Similarly, because signal intensity often varies in an unpredictable manner, signal identification based on intensity may also result in significant identification errors.

A U.S. patent of Thomas Stockham and Jeff Ives (U.S. Pat. No. 5,273,632) discloses an alternate method for base identification using blind deconvolution ("BD"). This patent is incorporated by reference herein in its entirety. The method of Stockham and Ives uses blind deconvolution to deblur information-containing signals in chromatographic data. This method, however, is significantly limited in the following manner. First, it relies on data derived from scanned autoradiogram image data. Second, the method requires user input of the BD filter bandwidth and programmer alterations to various thresholds. Third, the Stockham and Ives method does not adequately deal with lane to lane mobility differences. Fourth, the insertion/deletion and correction logic was too simple. Fifth, the putative peak detection was based on thresholds, and therefore, could miss band detections when band amplitudes dropped below the threshold. Sixth, the method of Stockham and Ives lacked the ability to align and merge adjacent sample segments. Finally, that method lacked band quality measures useful in automatic data routing and or sequence assembly.

SUMMARY AND OBJECTS OF THE INVENTION

The present invention includes a method and apparatus for the detection and analysis of information-containing signals in chromatographic data. The invention also includes a method and apparatus for detecting and sharpening signal peaks in chromatographic data. It is an advantage of the present invention that a chromatographic data from a wide variety of separation processes can be analyzed. Such separation processes include, but are not limited to, gel and capillary electrophoresis.

The present invention includes the steps of preprocessing signal data, reading successive sample segments, selecting blocks of high quality sequence and then producing traces of aligned high quality sequences. It is an advantage of the present invention that the chromatographic data may include single fluor samples fractionated in multiple lanes and multiple fluor samples fractionated in single lanes.

It is an object of the present invention to provide a method for preprocessing chromatographic data by baseline subtracting background noise. It is an advantage of the present invention that the method of baseline subtraction may be varied according to the type of chromatographic data being analyzed. It is a further advantage of the invention that sparse chromatographic data may be interpolated during preprocessing.

It is an object of the present invention to read the preprocessed signals in successive sample segments. It is an advantage that the sample segment size may be sufficiently large to provide for rapid and efficient signal analysis.

It is an object of the invention to provide a method and apparatus for detecting information-containing signals which are not uniformly distributed in the chromatographic data. This analytic technique uses iterative blind deconvolution to determine band frequency in sample segments. It is an advantage of the invention that the filter-band width is automatically varied during iteration to optimally detect the signals in the preprocessed chromatographic data. It is a further function of the invention to detect and correct signal data derived from chromatographic data which have segments which are short in one or more signal types (for example, "band-lite" signals).

It is an object of the present invention to provide a method and apparatus to detect and correct for mobility differences. It is a feature of the invention that mobility differences are corrected using a Monte Carlo alignment rather than using band position or spacing information. It is an advantage of the present invention that the Monte Carlo alignment is an iterative process to optimize signal alignment.

It is an object of the invention to enhance band detection using fuzzy logic. It is a feature of the invention that band detection is performed using fuzzy logic blocks, each block providing a particular method of data analysis. It is an object of the invention that each fuzzy logic block may be optimized for a particular analytic function.

It is an object of the present invention that the invention may optionally provide a quality measure for each signal. It is a feature of the invention that the quality measure can be utilized during subsequent alignment steps. It is an advantage of the invention that the quality measure can provide left and right cutoff point to limit subsequent analysis to data above a given quality measure.

These and other objects, features and advantages of the invention will be clear to a person of ordinary skill in the art upon reading this specification in light of the appending drawings.

BRIEF DESCRIPTION OF THE DRAWINGS

FIG. 11 depicts a flow chart of the GapCheck fuzzy logic block of FIG. 5.

FIG. 11A graphically illustrates the subject matter of the flowchart of FIG. 11.

FIG. 14B depicts a flow chart of the Monte Carlo Alignment function of FIG. 4.

FIGS. 14, 14A, 14C and 14D graphically illustrate the subject matter of the flowchart of FIG 9.

DETAILED DESCRIPTION OF THE PREFERRED EMBODIMENT

The present invention provides a method and apparatus for detecting and analyzing information-containing signals in chromatographic data. In the preferred embodiment, the invention analyzes chromatographic data from DNA sequence analysis machines employing various and sundry imaging techniques, including autoradiograms, four lane-single fluor, and single lane-four fluor data. The invention further includes general and dedicated apparatuses for performing the invented method. Finally, the invention also includes a kit comprising one or more of the following components in combination with the invented method: a DNA sequence apparatus, signal detection apparatus, information storage devices for preserving chromatographic data before, during and after analysis, and output devices for displaying the analyzed sequence information.

For DNA sequence analysis, the invented method takes as input the output from a DNA sequencing apparatus and returns the called sequence, aligned traces, and band metrics for each called base. After each sample segment is read, its called sequence, aligned traces, and band metrics are joined to previous read segments. After an entire ladder has been read, a final step analyzes each called base's metrics and assigns a quality value. The quality values are used to identify the largest block of high quality sequence and establish left and right cutoff values. If a "preamble" sequence is available, the base calling software will attempt to locate the preamble in the called sequence and set the left cutoff value beyond it. Such preamble sequences may include primer sequences or known sequences which are to be excluded from the collected data. This latter step improves the chance that the sequence called by this software would merge with the least amount of human intervention.

The following sections provide a detailed description of each function of the invented method. The illustrative embodiments of the invention exemplify the application of the useful characteristics discussed below, and further reference to these and other useful and novel features is made in the following discussion of each illustrative embodiment. These exemplary embodiments are intended to limit neither the scope of the method and apparatus that are needed for performing the invented method.

Figure 1:
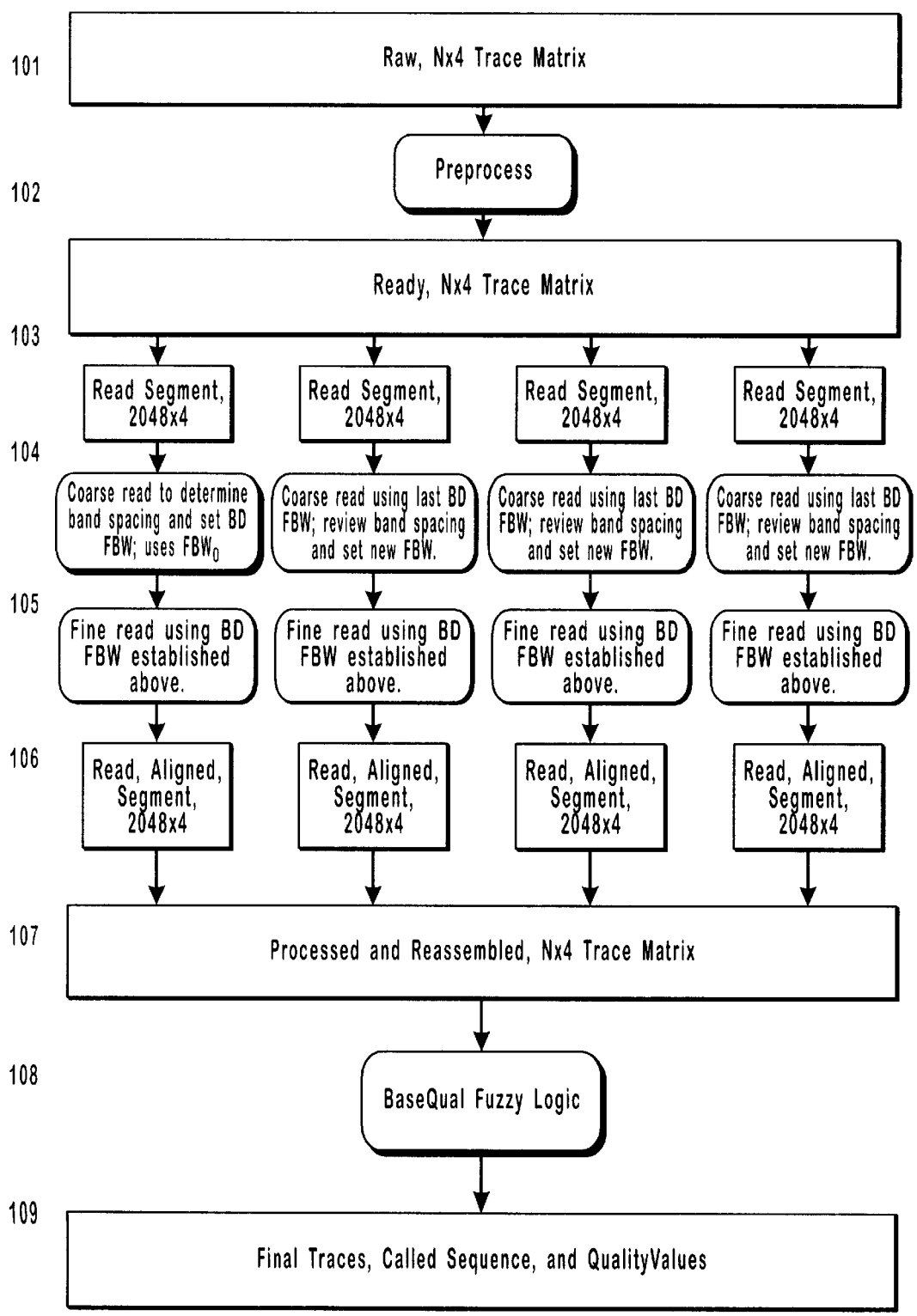
FIG. 1 depicts a flow chart for the invented base calling method.

Referring to FIG. 1, the invented base calling software first performs a preprocessing step 102 on the input data set 101. Preprocessing can include spectral separation, background subtraction and interpolation of input data set 101. The preprocessed data set 103 then enters Steps 104–106, which reads successive sample segments of the preprocessed data. The sample segments 104 may be any suitable size which provides efficient signal analysis. In the most preferred embodiment of the invention, the first segment is 2048 scanline samples. Subsequent segments are also 2048 samples, swith 148 samples overlapping the previous segment. The following description is based on the most preferred sample segment size, although the scope of the invention is not intended to be limited to that segment size.

Each sample segment 104 is first analyzed to estimate the coarse band spacing. Subsequently, the segment 104 is analyzed at second time 106 to refine the predicted band spacing. The band spacing drives the selection of the reconstruction filter employed during blind deconvolution. Band spacing and filter band width are inversely related. Once a sample segment of 2048 scanlines is read twice (a refined sample segment) and its band spacing measured and normalized for that 2048 scanline segment, the next sample segment of 2048 samples is read. The next sample segment overlaps the previous segment by 148 scanlines (or about 15 nucleotide bases) to establish the frame and relative positioning of adjacent segments. Subsequent segments 104 are similarly processed until the final sample segment 104 is reached. If fewer than 2048 scanlines are available in the original data set, then pseudo-random noise is generated to fill the sample segment to the required 2048 samples. Pseudo-random noise is preferred because sources of non-random noise will cause improper processing during the blind deconvolution and alignment steps.

Once all sample segments have been processed (read twice, normalized and the segments aligned), the processed and aligned data is analyzed in three fuzzy logic blocks. Fuzzy logic allows multivalued logic to enhance peak detection. By using fuzzy logic, a gap is "somewhat big," a band is "not so tall." Fuzzy logic also provides logic operators (for example AND, OR, NOT). Each fuzzy logic block in the base calling method provides a particular analysis of its data. The logic blocks operate on normalized input data and essentially classify each band based on absolute and relative criteria which are based on the band's neighboring bands. For example, fuzzy logic block 108 analyzes each base, its upstream context and assigns a quality value to each called band (base identity). Following the assignment of quality values, fuzzy logic block 108 also identifies the largest block of high quality data in the processed and aligned data 107. The right and left cutoff points for the high quality data block are recorded and set as left and right cutoff points. The output data set 109 includes the finished traces, the called bases with their assigned quality values and the suggested left and right cutoff points. Output data set 109 can optionally be visually enhanced to normalize all bands to about the same band amplitude and to remove the saw tooth appearance of the non-visually enhanced traces.

A. Preprocessing

Figure 2:
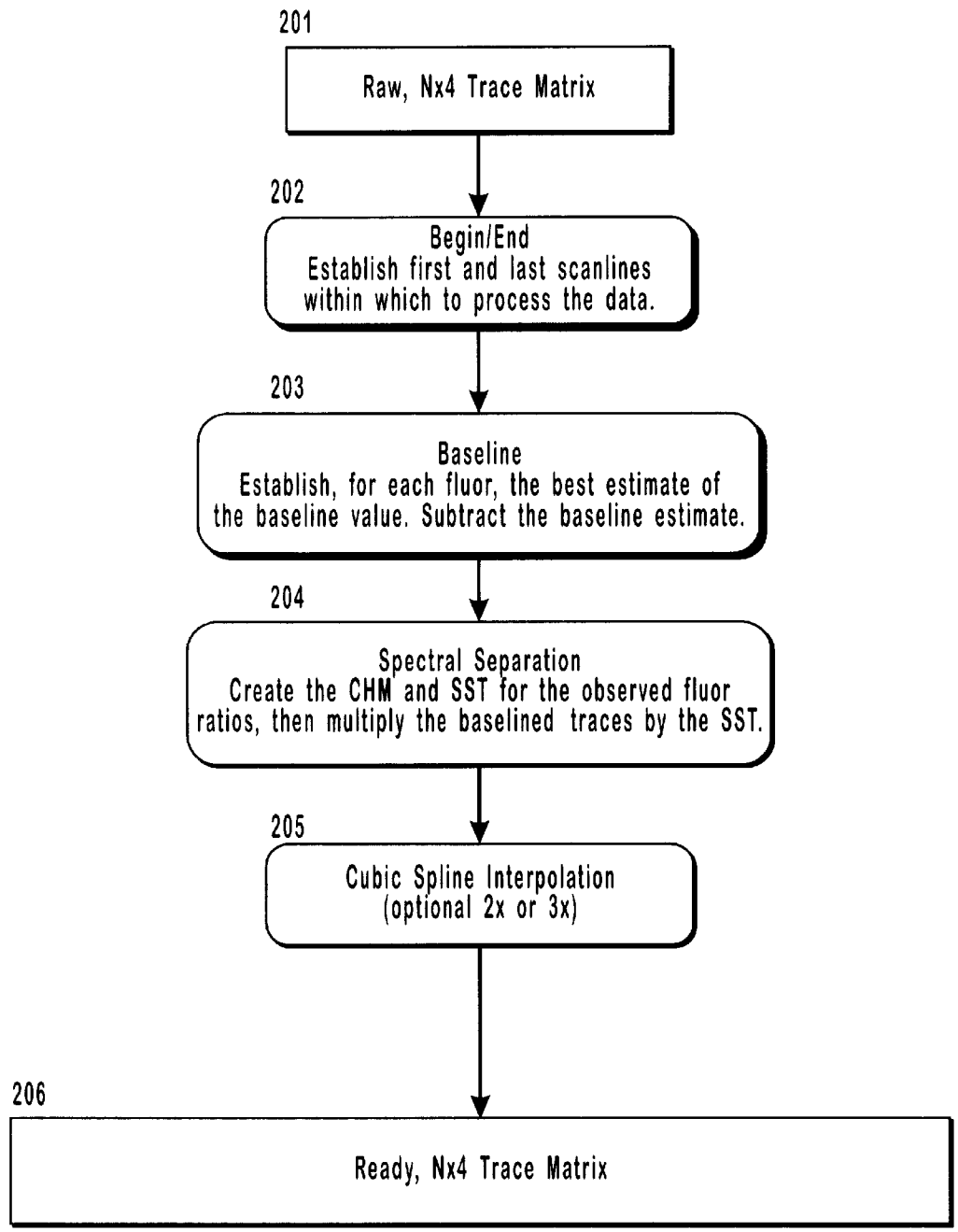
FIG. 2 depicts a flow chart of the preprocessing step of FIG. 1.
Figure 2A:
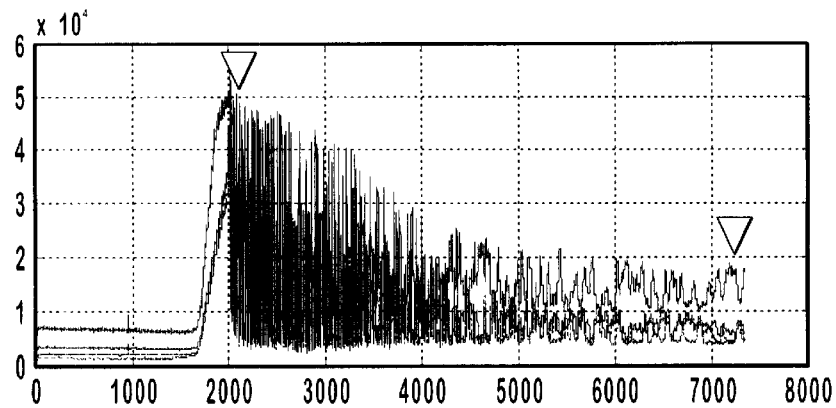
FIG. 2A depicts "Begin/End" step of FIG. 2 as applied to a data signal.
Figure 2B:
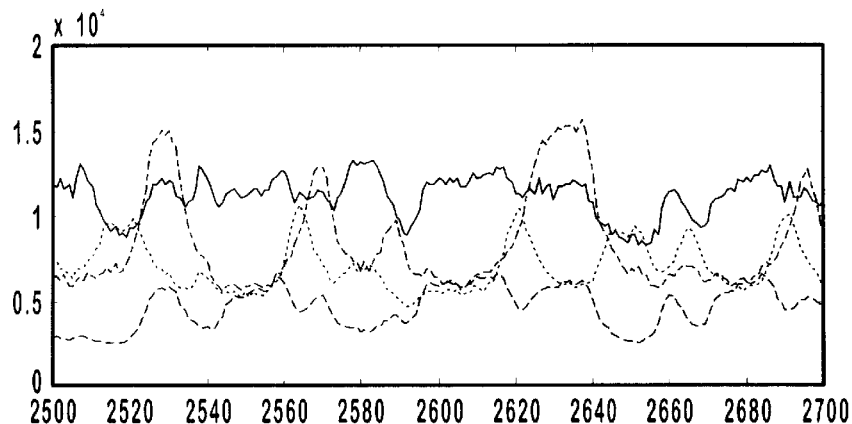
FIG. 2B and 2C depict the signals involved in the "Baseline" step of FIG. 2.
Figure 2C:
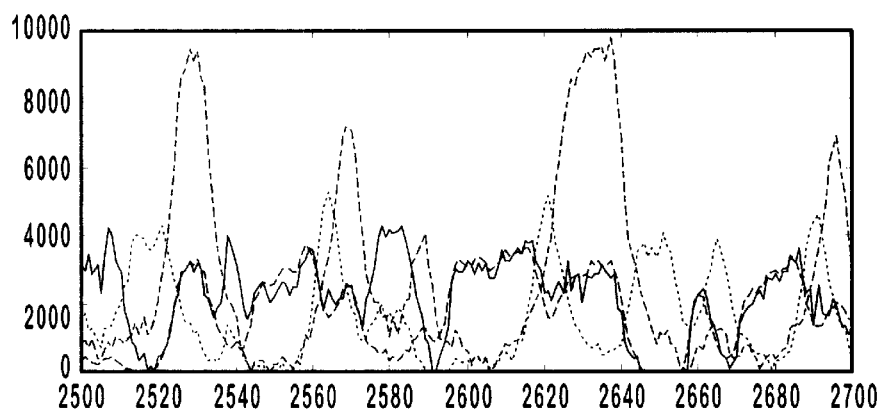
Figure 2D:
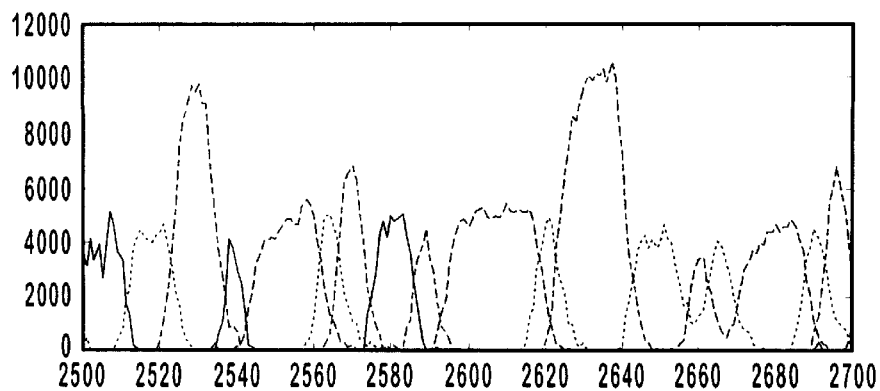
FIG. 2D depicts the "Spectral Separation" step of FIG. 2.

Referring to FIG. 2, input data set 201 is an 2048×4 trace matrix. The first step is to established Begin and End points by analyzing input data set 201 for the first scanlines containing above-background signal and for the last scanlines containing such signal (See trace 202a as an example.) Large signal spikes, due to artifacts such as primer peaks, are excluded.

Figure 23:
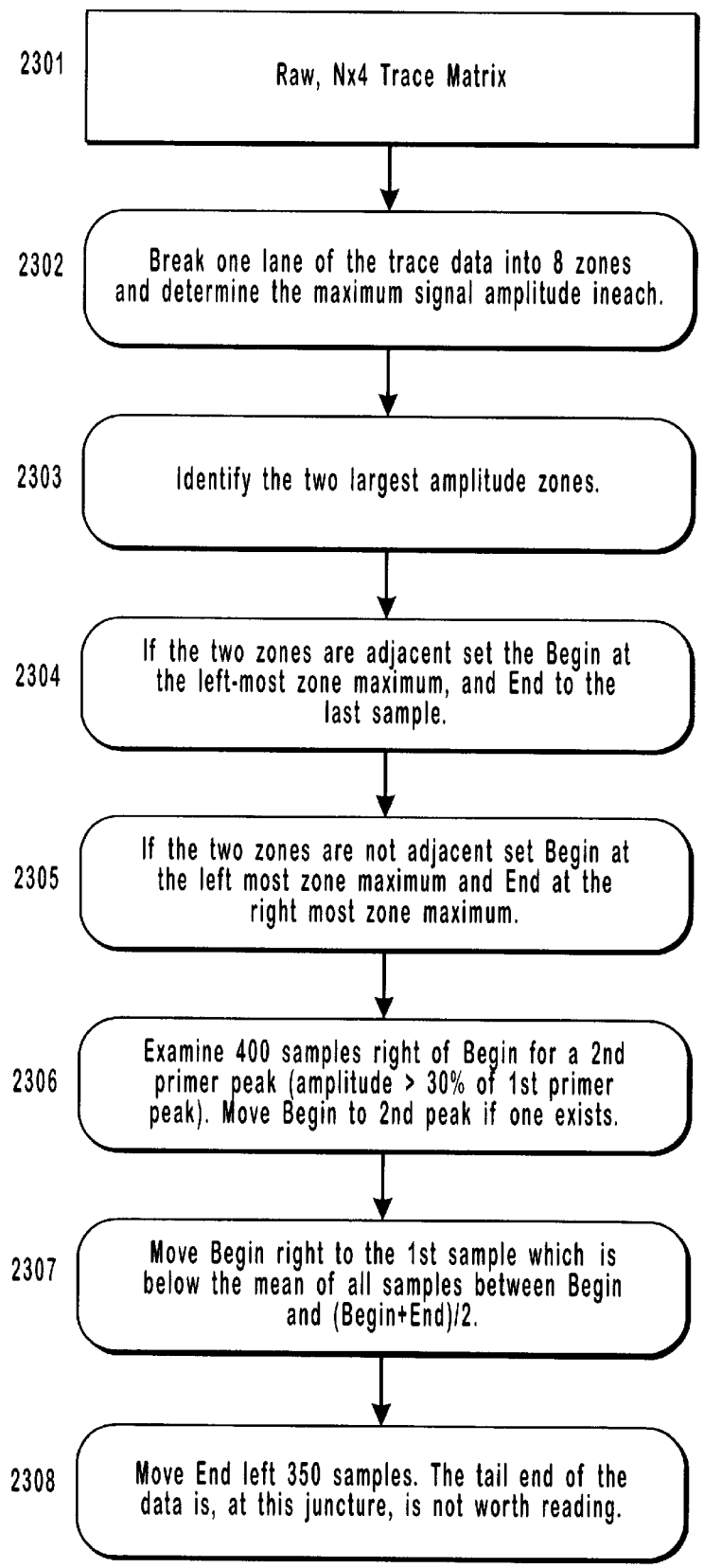
FIG. 23 depicts a flow chart of the Pre-Processing Begin/End Detection of FIG. 1.

Referring to FIG. 23, the Preprocessing Begin/End subroutine identifies the Begin and End points based on signal amplitude. The Begin and End points define the usable signal for subsequent operations. Usable signal typically begins just left of the largest left-most signal amplitude (the so called primer peak), and continues until either the end of the sample segment data or another region of large signal amplitude is encountered. (The latter peak is typically called a biostreptation peak.) More specifically, steps 2302 through 2305 identify the putative start and end points by breaking the sample segment into zones and determining the maximum signal amplitude in each zone. Step 2306 determines whether a second primer peak is present. If the second peak is present, Step 2306 sets the Begin point at the second primer peak. Steps 2307 and 2308 make final adjustments to the Begin and End points, setting the Begin point to the first sample with amplitude below the mean of the first half of the signal, and setting the End point back 350 samples from end.

Referring to FIG. 2, the baseline of the Preprocessed Begin/End data 202 is then determined at Step 203. A single baseline is established for each fluor of the Preprocessed Begin/End data 202. The baseline is subtracted from Preprocessed Begin/End data 202 to generate a baseline subtracted data set 203. For example, after baseline subtraction, the localized data set 203a becomes baseline subtracted data set 203b. In a more preferred embodiment of the invention, a single baseline is established based on data from all lanes. This best determines the baseline beneath a run of poorly resolved bases in one lane. Currently available DNA sequence data precludes this embodiment because no two fluors reliably a common baseline.

Figure 22:
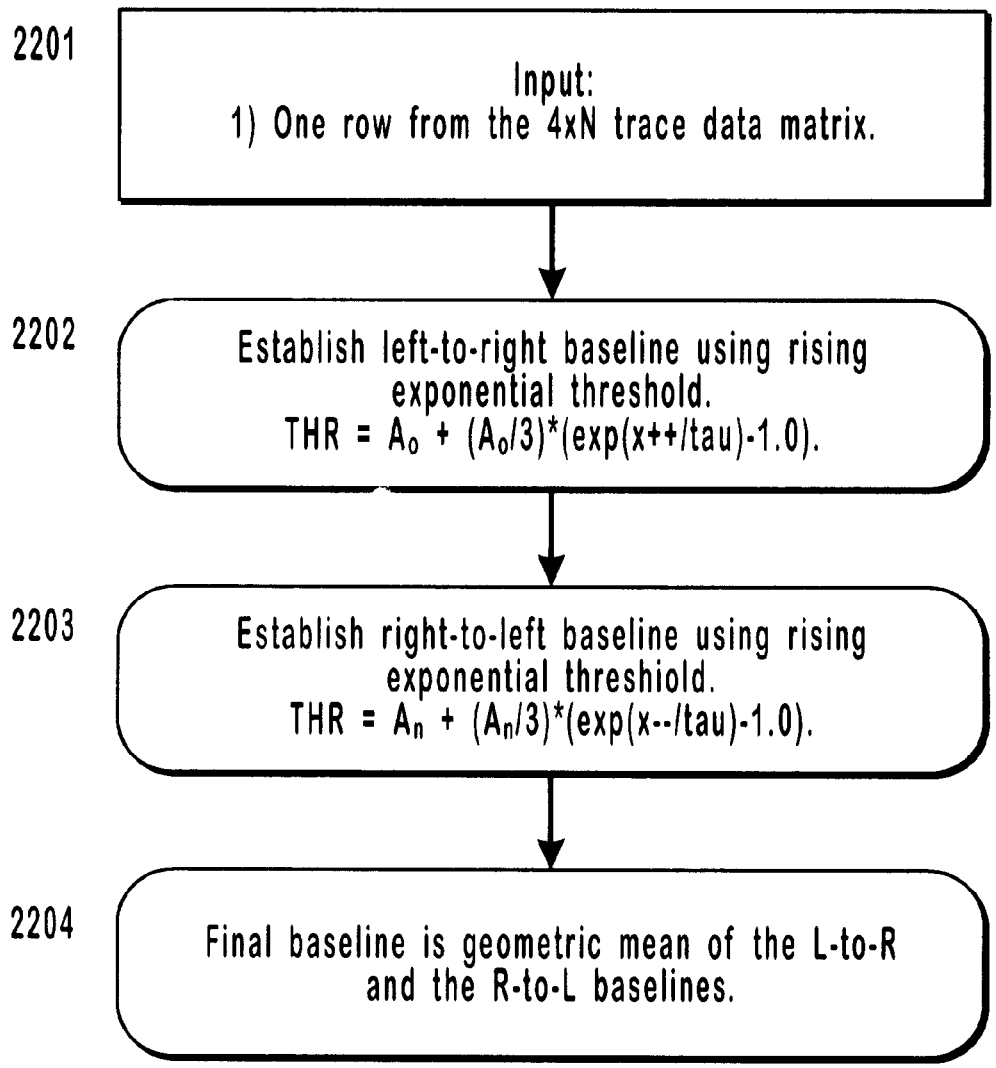
FIG. 22 depicts a flow chart of the Baseline Substraction algorithm of FIG. 2.
Figure 22A:
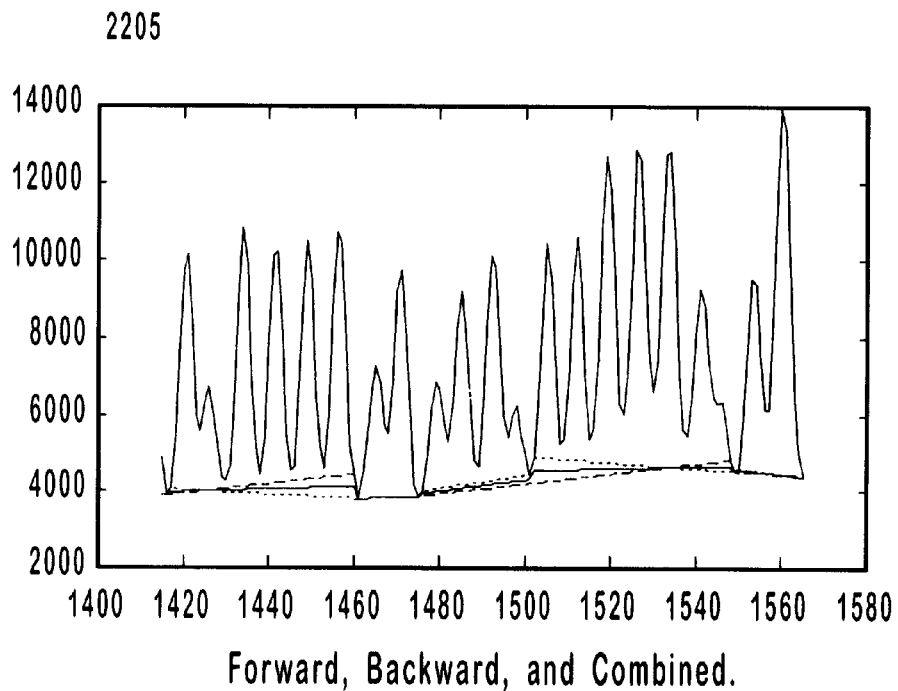
FIGS. 22A and 22B graphically illustrate the subject matter of the flowchart of FIG. 22.
Figure 22B:
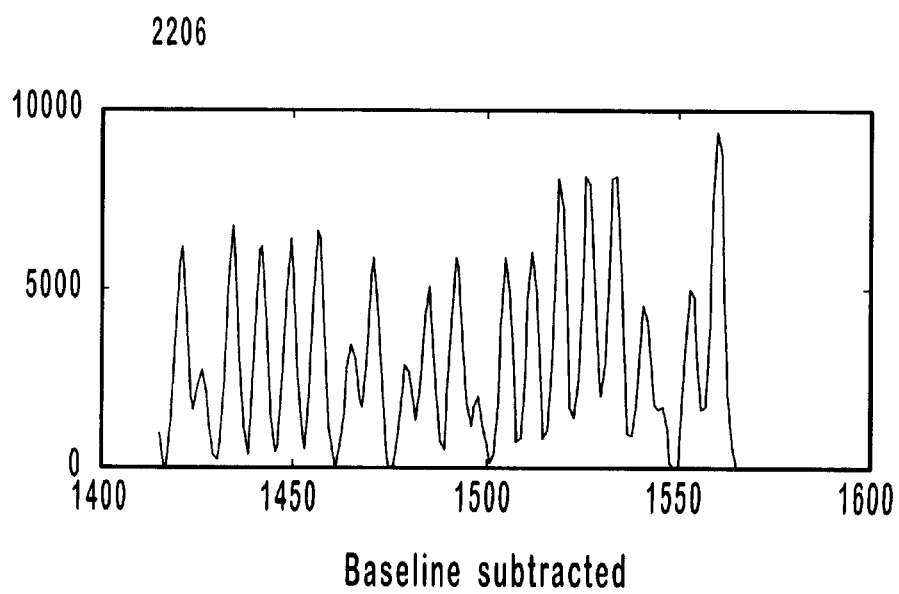

Referring to FIG. 22, the baseline can be established by estimating the baseline of the Preprocessed Begin/End 2201. In the working embodiment, each trace lane is processed twice using a rising exponential threshold. One pass is made from left to right (establishing one baseline) (Step 2202), and the next pass is from right to left (establishing another baseline) (Step 2203). By taking the geometric mean of the two baseline approximations a fairly natural subtrahend is produced. (See sample traces 2205 and 2206.)

To establish a baseline approximation using a rising exponential threshold, a threshold is initially set to the lowest point found within the first 10 samples. As each successive sample is considered, the threshold is incremented by an exponential which slowly ramps upward. When a subthreshold sample is encountered, the baseline between the previous subthreshold point and the current point is taken to be a line segment between the points. The threshold is reset to the new subthreshold sample value and the process continues. If, after 100 samples no subthreshold point has been found, a 100 point segment of the baseline is computed (again, piecewise linear), and the rate of rise of the exponential is increased. The exponential is calculated to rise by ⅓ the amplitude of the most recent subthreshold point over a span of 75 samples.

Following baseline subtraction, baseline subtracted data set 203 is preferably spectrally or leakage separated. This step markedly improves the quality of capillary electrophoresis data. For slab gel data with a signal to noise ratio of 2.0 or less, separation step 204 significantly improves data quality, such that unreadable data can become readable. The separation step 204 is preferably performed during preprocessing without user input.

For four fluor-single lane data, the baseline-subtracted data set 203 is spectrally separated. For single fluor-four lane data, data set 203 is leakage separated. For either separation, the separation algorithm 204 builds a characteristic matrix (CHM) which is used to perform the separation. For spectral separation, the characteristic matrix captures the spectral cross-talk ratios in four fluor data. For leakage separation, the characteristic matrix is generated from the ratio of leakage from the signal in the center of the lane in question to the signal in adjacent lanes. For capillary electrophoresis data, the ratios are measured at "peak center." For slab gel data, all data points are used to generate the characteristic matrix.

A separation matrix is calculated according to the formula, $$SST = inv(CHM * CHM^T)^{-1}$$

where the columns of CHM hold the ratios for each respective lane. The ratios are normalized so that the largest element in each column has a value of one. The result of separation 204 is a separated data set 204.

Processing steps 104–106 are optimally performed on preprocessed data 206 containing at least 8 scanlines (samples) per band. To increase the number of scanlines per band, a baseline subtracted data set 203 or a separated data set 204 may optionally be enhanced to double or triple the number of samples using cubic spline interpolation 205.

B. Reading

Figure 3:
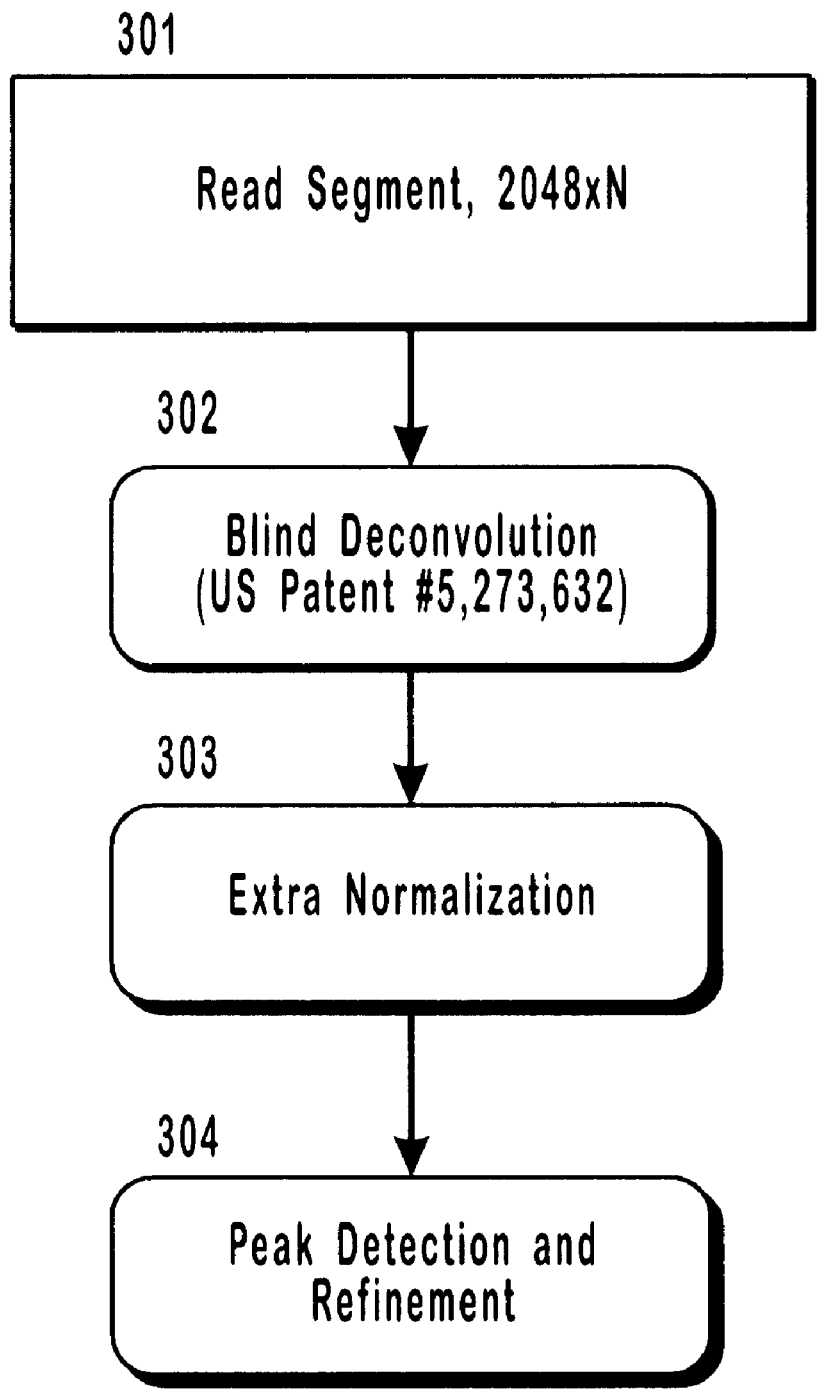
FIG. 3 depicts a flow chart of the base reading step of FIG. 1.
Figure 3A:
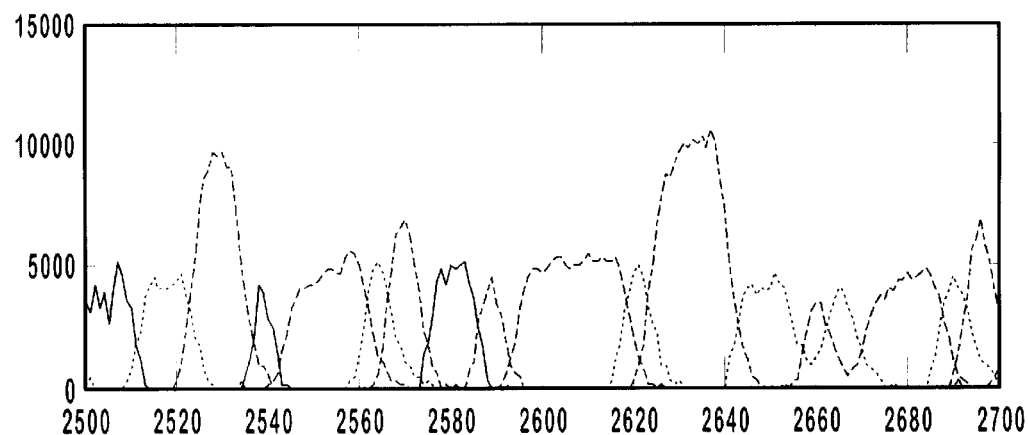
FIG. 3A and 3B depict the signals involoved in the "Blind Deconvolution" step of FIG 3.
Figure 3B:
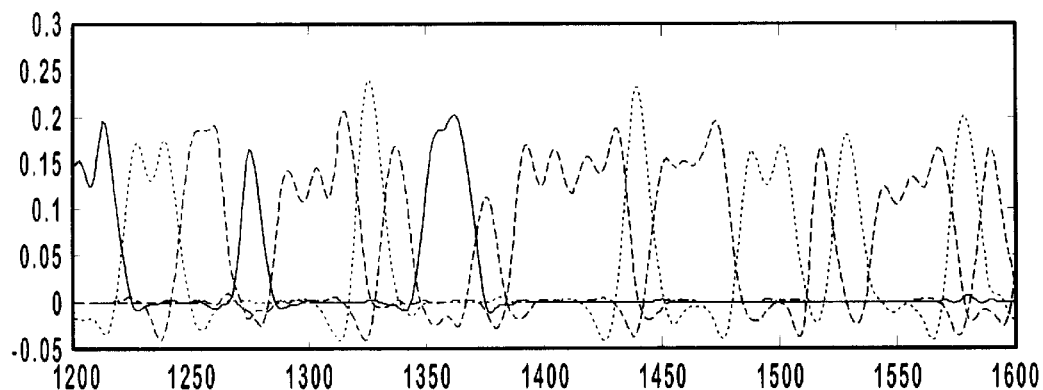
Figure 3C:
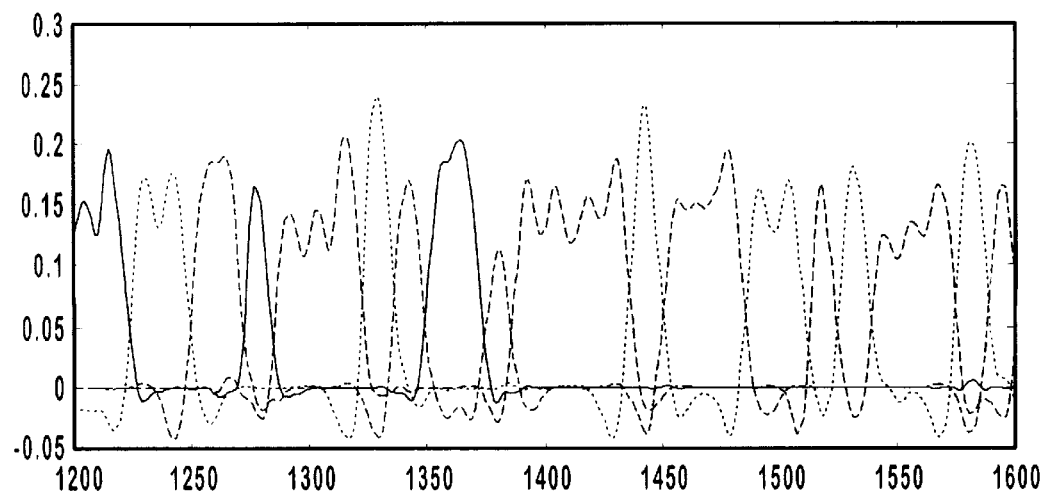
FIG. 3C depicts the signal involved in the "Extra Normalization" step of FIG. 3.

Referring to FIG. 3, the exemplified reading step analyzes sample segments 301 of 2048 scanlines. Each sample segment 301 first undergoes blind deconvolution 302 to cancel the effects of an unknown laurentian blurring function and to normalize the amplitudes of the traces. Blind deconvolution is described in the U.S. Patent to T. G. Stockham and J. T. Ives (U.S. Pat. No. 5,273,632), which is incorporated by reference herein.

The presently invented method includes the following improvements over the method of Stockman and Ives. The first 2048 samples are blind deconvolved with an initial narrow-band guess for the filter band width ("FBW") value. The narrow-band guess is made so that the initial reading does not overestimate the band density along the sample segment. Given the resulting conservative estimate of the band density, a subsequent, more apt FBW is chosen and the segment is reread using it. The FBW chosen for the second read of each segment also serves as the FBW used for the 1st read of following segment. This iterative approach to determining the best FBW has proven invaluable in practice; the band densities may vary from about 6 samples/band to about 50 samples/band, and do so not only within a given ladder but also from sequencing run to sequencing run. In the preferred embodiment of the invention, the method is adaptable to a wide range of acceptable inputs.

The invented method includes a means for selecting the filter band width (FBW) during blind deconvolution 302. In the working embodiment median band spacing is mapped to a filter band width value using the following equations:

$$K = 2 * \sqrt{\ln(0.23)/-0.5}$$

$$FBW = 0.5 + (K/med\_band\_spacing) * (2048/(2*\pi))$$

The blind deconvolution step 302 deblurs the signal and normalizes its amplitude. Following blind deconvolution, an extra-normalization function 303 adjusts band spacing due to mobility differences in the samples. Extra-normalization 303 also corrects for the tendency of blind deconvolution to create spurious bands, especially in regions of mono-, di- or tri-nucleotide repeats where one or more lanes are band-lite for extended regions.

Figure 4:
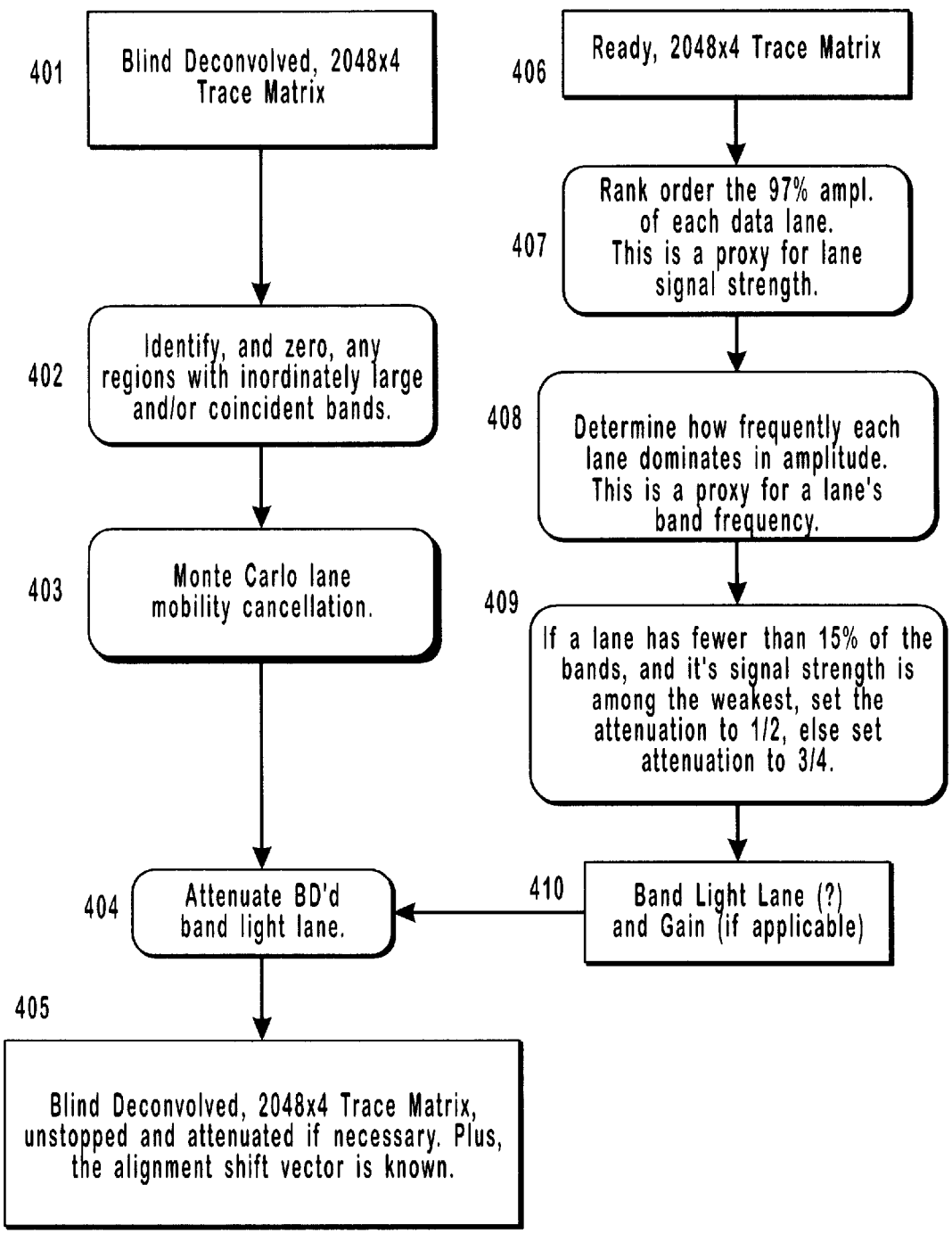
FIG. 4 depicts a flow chart of the extra-normalization step of FIG. 3.

Referring to FIG. 4, extra-normalization 303 corrects two types of artifacts created by blind deconvolution. Path 406–410 cancels artifacts created in band-lite lanes. Briefly, the blindly deconvolved data set 406 is scanned for band-lite lanes by comparing the relative lane signal strengths and the relative lane band frequencies. The proxy used for the lane signal strength analysis is the $97^{th}$ percentile signal amplitude found in each lane. The proxy used for the band frequency is the proportion of the signal over which the lane in question has the largest signal amplitude. If a lane has less than 15% of the total bands found in all four lanes in a sample segment, and if the band amplitudes are low relative to the other lanes, the amplitudes of the bands in that lane are attenuated. If the band amplitude is lowest, those amplitudes are attenuated by one-half. If the band amplitude is above the lowest, the amplitudes are attenuated to three-quarters of the original band amplitude. In contrast, in ideal sequence data, where A, G, C, and T are equal in frequency, each trace should dominate 25% of the time.

Extra-normalization path 401–403 corrects for mobility differences between lanes and performs the actual band-lite attenuation 404. Briefly, the blind deconvolved data set 401 is analyzed to identify any regions with inordinately large or coincident bands. These regions are set to zero (base-line). If these regions were not set to zero the Monte Carlo alignment algorithm 403 would produce an aberrant alignment which focused on separating them.

Referring to FIG. 14, mobility shifts are most noticeable in the autoradiogram and single fluor-four lane data particularly near the edges of the gel. The prior method of Stockham and Ives described an algorithm which attempted to align the lanes by driving the band spacing to as nearly a uniform value as possible. This approach was limited because, without proper alignment, many true bands would go undetected because they were shadowed by other bands. The algorithm attempted to normalize spacing between detected bands, yet the algorithm knew of only a simple majority of the bands present in the data.

The present invention uses an algorithm which does not use band position or spacing information. Instead, the present invention seeks to maximize the integral of the "envelope" of all four lanes of data when they share a common baseline. Alignment is accomplished using a Monte Carlo search of a 3D space, where the x-axis defines the relation between the A and G lanes, the y-axis defines the relation between the AG relation and the C lane, and the z-axis defines the relation between the AGC relation and the T lane. An initial set of possible alignments are chosen, each triple is applied to the traces to be aligned, and the integral of the resulting envelope is calculated. A subset of the triples, those yielding the largest integrals, are then refined. The triple which yields the lowest integral is removed from the set under consideration. It is replaced by a triple which results from a random alteration of the triple which yields the largest integral. When either a maximum number of iterations has occurred or the variation within the set of high integral triples has reached a suitably low value, the highest yielding triple is chosen as the alignment vector for the segment under consideration.

More specifically, the search is conducted in a three dimensional space, where the x-axis specifies the offset between $trace_1$ and $trace_2$, the y-axis specifies the offset between the $trace_{1,2}$ registry and $trace_3$, and the z-axis specifies the offset between the $trace_{1,2,3}$ registry and $trace_4$ (See illustration 1401). The algorithm employed was originally described by W. L. Price in *The Computer Journal*, Vol. 20, No. 4, which is incorporated by reference herein.

Initially, a set of putative alignment solutions 1401 is generated. The addresses of the lattice points of 6 concentric cubes centered about a point in the space are used as the initial alignment solutions. The first time the procedure is used the central point of the concentric cube lattice is the origin ($x_0=0$, $y_0=0$, $z_0=0$). Subsequent calls can either continue to center the lattice on the origin, or they can bias the search by centering the lattice on the previous alignment solution ($x_{n-1}$, $Y_{n-1}$, $z_{n-1}$).

Each alignment guess is converted into a shift vector of four values, wherein one value is 0. Each trace in the matrix is shifted by the amount specified in the shift vector, the envelope of the shifted traces is obtained (the maximum value of the four trace values found at each position along the traces), and is summed. The sum represents the integral of the envelope produced by the alignment guess. A low integral value represents a poor alignment (see, e.g. illustration 1402, where the bands are aligned behind others, not arranged "shoulder to shoulder"), whereas a high integral value corresponds to a good alignment (see, e.g. illustration 1407, where all bands are fully exposed, arranged "shoulder to shoulder").

Once all alignment guesses have been evaluated, the worst alignment solution is replaced by a small, random perturbation of the best alignment solution 1405. The new alignment solution is evaluated, and the process repeats, replacing the new worst alignment with a perturbation of the new best alignment. Eventually, the set of points in the 3D space converge about the best alignment solution 1406.

Figure 5:
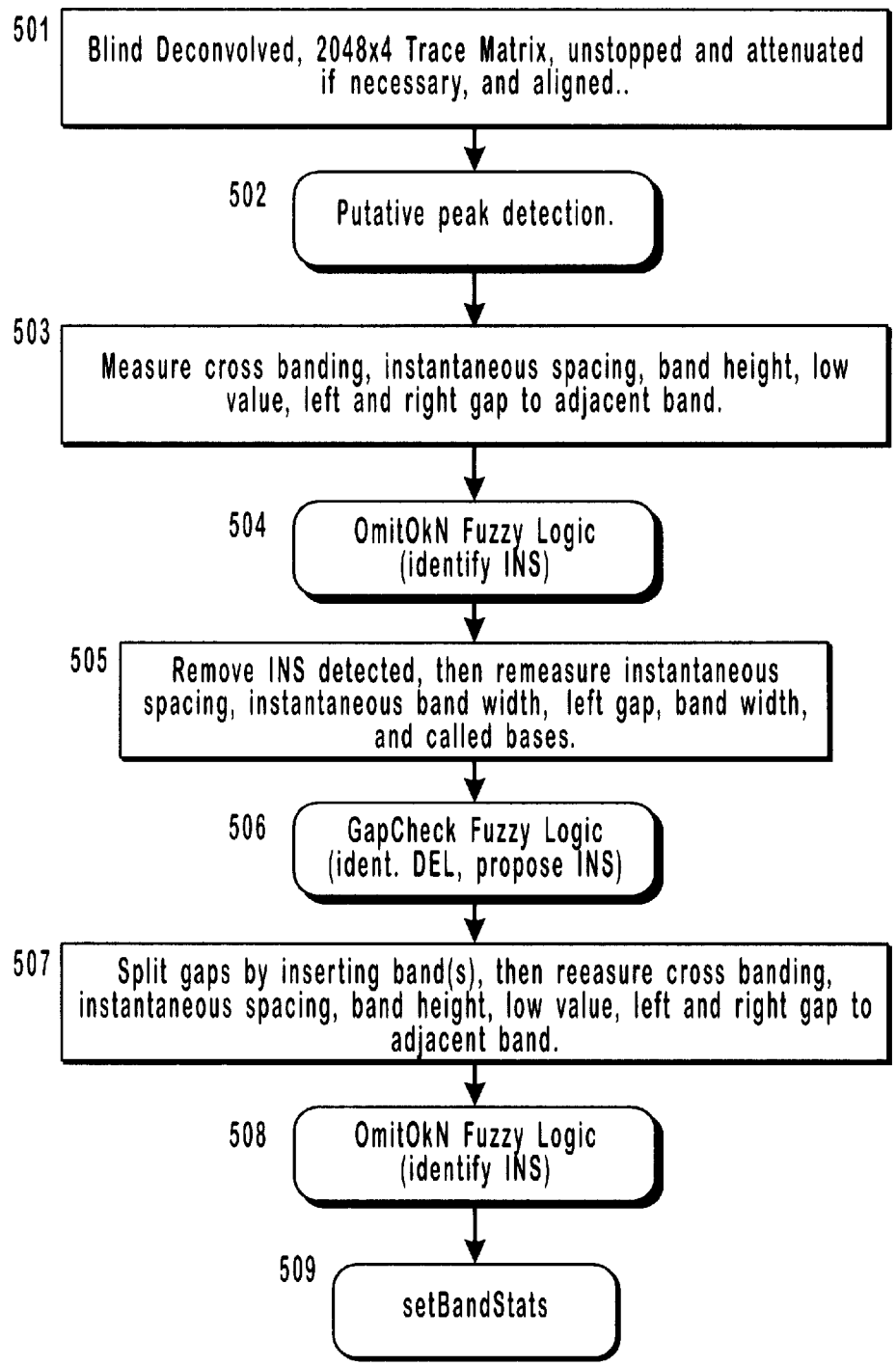
FIG. 5 depicts a flow chart of the peak detection and refinement step of FIG. 3.

Referring to FIG. 3, following extra-normalization 303, Step 304, peak detection and refinement, occurs. The aligned traces then undergo putative peak detection. Referring to FIG. 5, putative peak detection 502 is performed on the blind deconvolved, extra-normalized data set 501 (unstopped, attenuated and with the relative mobilities corrected). A trace envelope is first determined. The Stockham and Ives Patent described detecting peaks in each trace separately with thresholds derived from the underlying data. In the invented method, the trace envelope is peak-detected and no thresholds are employed. A peak is liberally defined to be a sample which is taller than either of its two neighbors. Subsequent processing culls this liberally defined putative peak list. This form of peak detection is both faster (one trace instead of four) and less prone to error (no subthreshold peaks). In contrast, the Stockham and Ives Patent required individual trace peak detection because its alignment algorithm attempted to determine lane alignment using peak location information.

To identify errors in putative band detection 502, including insertion errors, each putative peak's instantaneous spacing, cross banding, height, and spacing to adjacent bands is measured (Step 503). These observed band spacing measurements are fit with a quadratic curve. This quadratic fit is used as the expectation of the band spacing along the entire read segment. This approach to defining the expected band spacing is sufficiently general to handle segments where, as in the Stockham and Ives Patent, the average spacing is an adequate expectation, as well as segments where the spacing changes radically. In the invented method, more information was found necessary to sufficiently identify insertions and regions of deletions, and as a result, the invented method can resolve a series of insertions and deletions.

Figures 6, 6A:
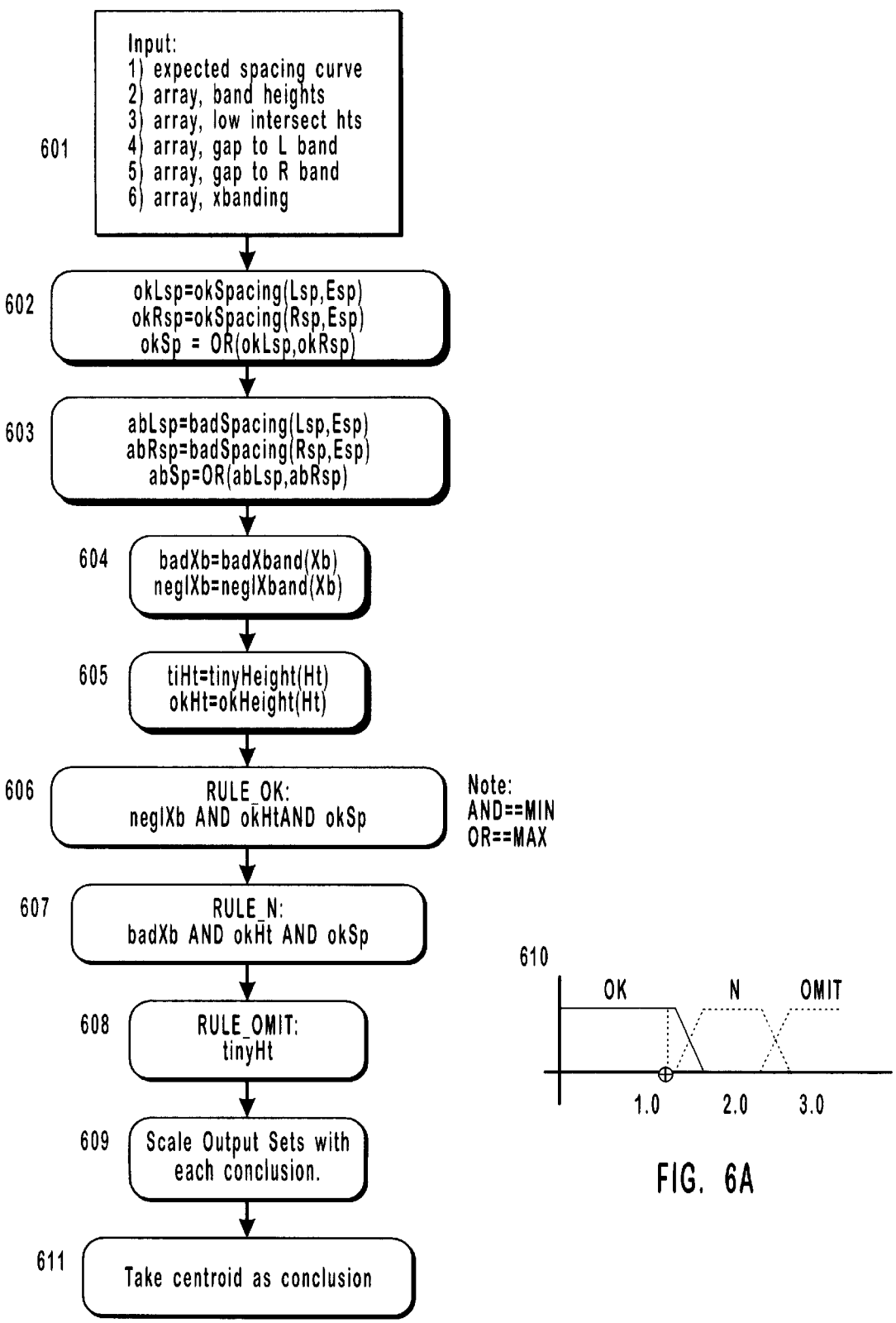
FIG. 6 depicts a flow chart of the OmitOkN fuzzy logic block of FIG. 5.
FIG. 6A graphically illustrates the subject matter of the flowchart of FIG. 6.

The first of three fuzzy logic blocks 504, OmitOkN Fuzzy Logic, is then used to identify bands which are most likely insertion artifacts of the band detection process. This block classifies the detections as OK, AMBIGUOUS or OMIT. The putative bands given the OMIT classification are removed from the putative peak set. Referring to FIG. 6, each band has several of its attributes 601 examined by this first logic block. If a band is where it ought to be with respect to either of its neighbors, then variable okSp is set "TRUE" (Step 602).

Figure 7:
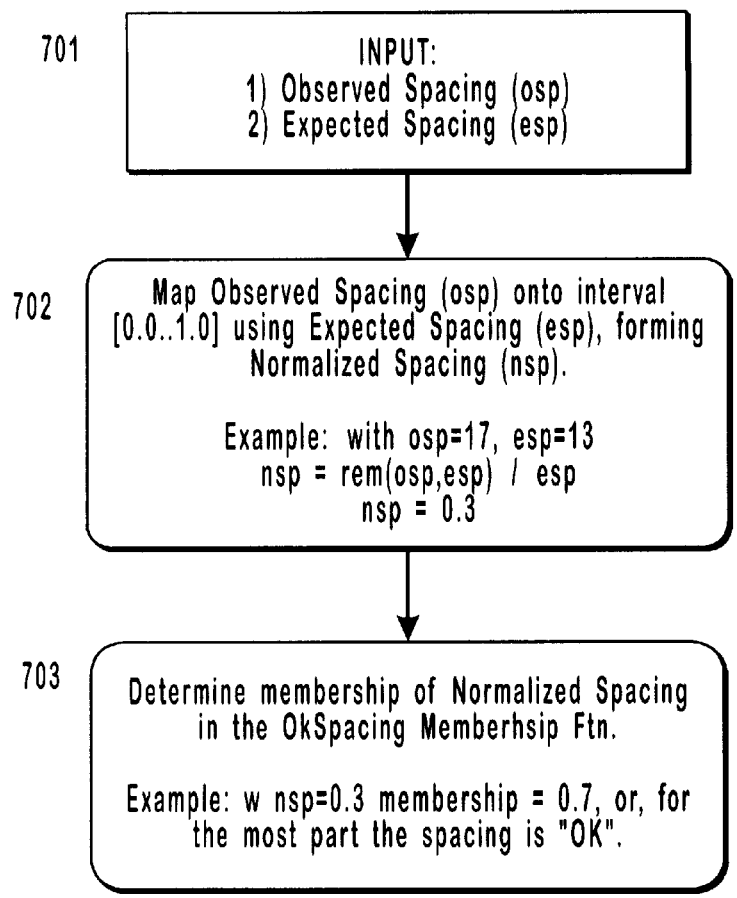
FIG. 7 depicts a flow chart of the OKSpMembership fuzzy logic block of FIG. 6.
Figure 7A:
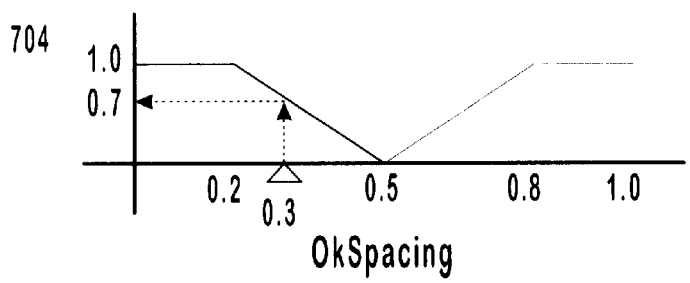
FIG. 7A graphically illustrates the subject matter of the flowchart of FIG. 7.

Referring to FIG. 7, the intent of the membership function for the OmitOkN Ok Spacing fuzzy logic block is to "accept" a spacing measurement which is an integer multiple of the expected spacing. Consequently, the observed spacing is normalized to a value on the interval [0 . . . 1] using its relationship to expected spacing (Step 702). In the example given in block 702, the normalized spacing of 0.3 is found to be OK with a truth value of 0.7 (Step 703 and Example 704). Given the vagaries of band migration, compressions, band shape (hence band peak position), and other factors, a peak spaced 17 from its neighbor when the expected spacing is 13 is neither ideal nor terrible.

Figure 8:
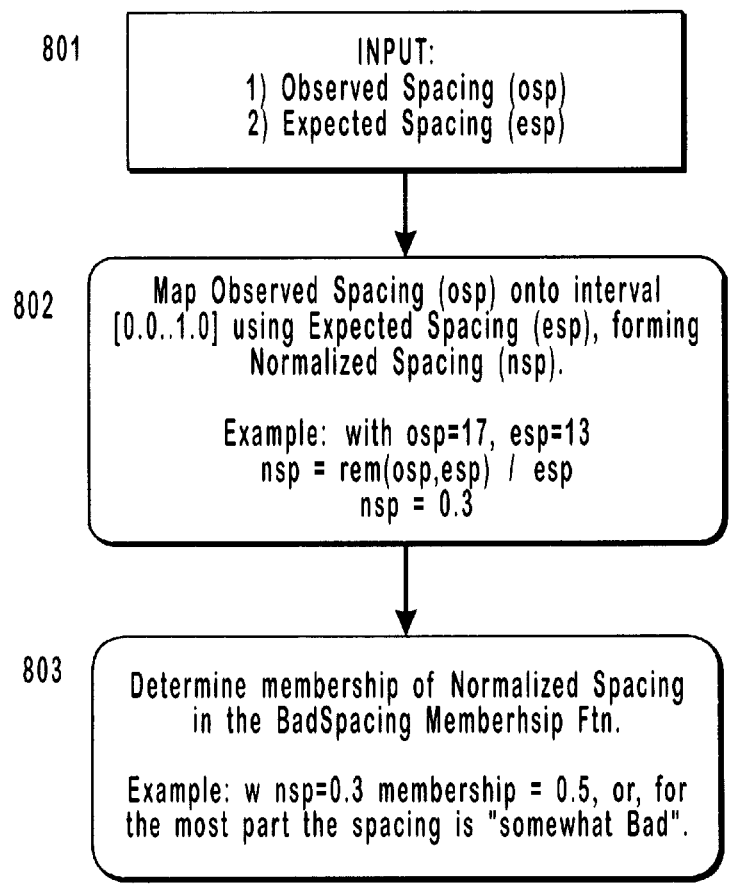
FIG. 8 depicts a flow chart of the OmitOkN Bad Spacing Membership fuzzy logic block of FIG. 6.
Figure 8A:
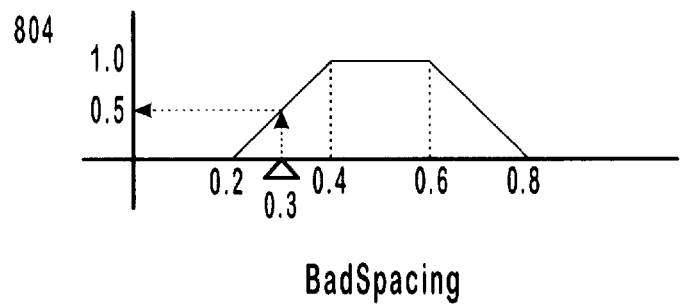
FIG. 8A graphically illustrates the subject matter of the flowchart of FIG. 8.

Referring to FIG. 8, for the OmitokN Bad Spacing fuzzy logic block, the intent of the membership function is to "deprecate" a spacing measurement which is not an integer multiple of the expected spacing. Consequently, the observed spacing is normalized to interval [0 . . . 1] using its relationship to expected spacing (Step 802). In the example given in Step 802-03 and Example 804, a normalized spacing of 0.3 is found to be BAD with a truth value of 0.5.; this spacing is not as good as it could be.

Figure 9:
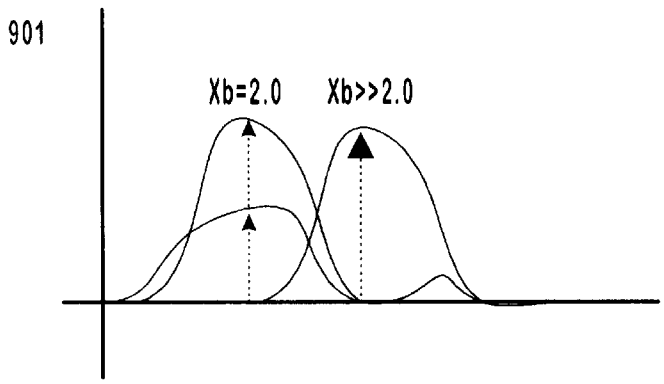
FIGS. 9 and 9B graphically illustrate the subject matter of the flowchart of FIG. 9A.
Figure 9A:
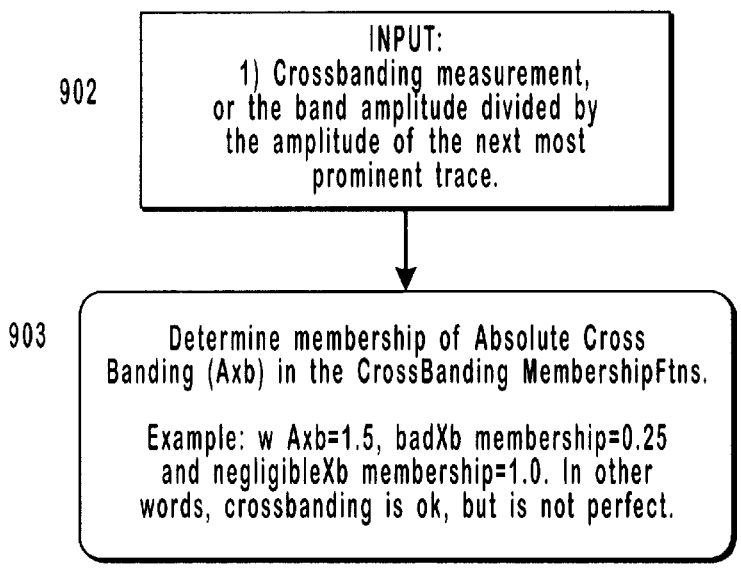
FIG. 9A depicts a flow chart of the OmitokN Cross Banding fuzzy logic block of FIG. 6.
Figure 9B:
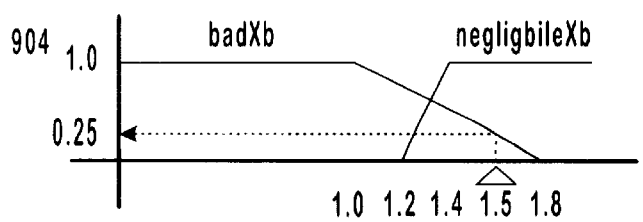

If a band is not where it ought to be with respect to either of its neighbors then variable abSp is set "TRUE" (Step 603). If the amount of "cross banding" (i.e. the amount of competition by two bands for a particular region of the read segment) is high, then variable badxb is set "TRUE" (Step 604). Similarly, if there is negligible cross banding then variable neglxb is set "TRUE". Referring to FIG. 9, cross banding designates the amount of competition for the scan-lines underlying a detected band. Bands of a dubious nature have wide ranging cross band ratios due to their apex's proximity to the baseline. However, compressions and stops, with significant amplitudes, can have their cross banding measured. The cross banding membership function is best used in identifying OK or AMBIGUOUS bands. In the diagram provided (Example 901), the first complex has two bands vying for the same location, with the second largest band having one-half the amplitude of the largest. The cross banding ratio (Step 902) is the amplitude of the largest band divided by the amplitude of the next largest band, or in this case Xb=2.0. In the second complex, where one band is clearly the band of choice, this ratio approaches infinity. In the example given in Step 903, with a cross banding ratio of 1.5, the badXb membership is 0.25, while the negligiblexb membership is 1.0; in other words, while a ratio of 1.5 is found negligible, the band legitimacy will be questioned.

Figure 10:
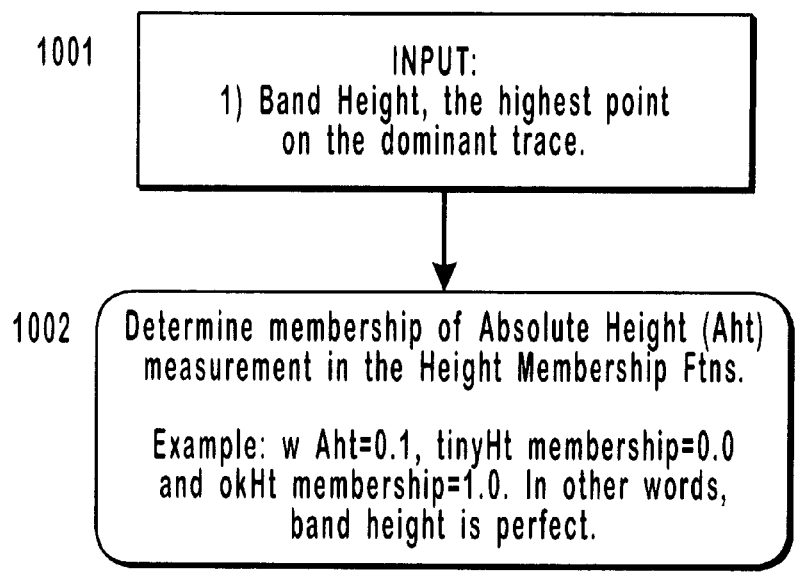
FIG. 10 depicts a flow chart of the OmitOkN Height fuzzy logic block of FIG. 6.
Figure 10A:
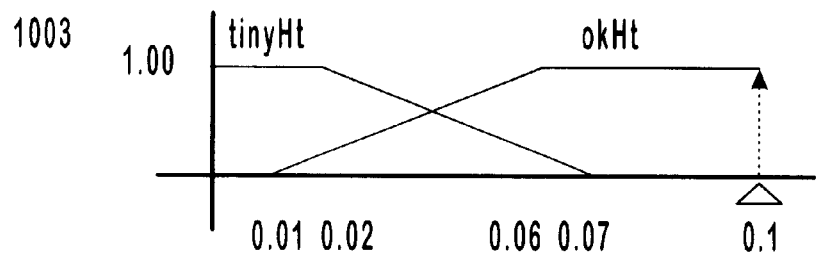
FIG. 10A graphically illustrates the subject matter of the flowchart of FIG. 10.

The band height is also categorized as either tiny or ok (Step 605). Referring to FIG. 10, for the height membership functions the membership sets are best customized for the general signal quality one observes from the machine providing the data. In the working embodiment a function of the median value of amplitudes measured where bands intersect determines the height membership function break points. In particular, the tinyHt function breaks at 0.4*med_intersect_pt and is zero by 1.1*med_intersect_pt. Similarly, the okHt function comes off zero at 0.5*med_intersect_pt and flattens off at 1.0 at 1.5*med_intersect_pt. The blind deconvolution process normalizes band amplitudes to interval [0 . . . 1], with most bands having a height in excess of 0.1. This example given is typical in that it begins deprecating a band based on its height when the height falls below 0.07. In the example given in Step 1002, the measured band height is 0.1 and has membership in okht of 1.0 and in tinyHt of 0.0. The band has, per this example of the sets, sufficient height.

These six variables then serve as input to fuzzy combinational logic. A significant advantage of fuzzy logic is that it works with and can resolve contradictions among rules involving these variables. Bands classified as OK are those with negligible cross banding and either OK height or OK spacing (Step 606). Bands classified as ambiguous exhibit bad cross banding and either OK height or OK spacing and little height (Step 607). Ambiguous bands are typically those where the band is correctly positioned with sufficient amplitude but significant cross banding (Step 607). Bands classified as clear insertions, and therefore to be omitted, are characterized by negligible height (Step 608). Cross banding is not considered when deciding whether a band should be omitted because usually insertions are made very close to the baseline where cross banding measurements are unreliable.

The strength of the rule firings is then used to scale the output sets (Step 609). In the example given (illustration 610), the output set OK is scaled with amplitude 1.0, output set N (ambiguous) is scaled with 0.25, and set OMIT is scaled with 0.0. Defuzzification, or obtaining a crisp (conclusion) value from the output rule sets, is achieved by calculating the centroid of the resultant "masses". In the example, the conclusion reached is that the band is OK (Step 611).

Referring to FIG. 5, following fuzzy logic block 504, each peak's instantaneous spacing, instantaneous band width, spacing to its left neighbor (left spacing), band width and called bases is remeasured (Step 505). These observed band spacings are fit with a quadratic curve which then serves as the expected spacing along the read segment. Similarly, the observed band width measurements are also fit with a quadratic curve which serves as the expected band width along the read segment.

The second fuzzy logic block 506, GapCheck Fuzzy Logic, then identifies bands, or gaps between bands, where one or more bands may need to be inserted to achieve the band spacing predicted by the quadratic fit. This block classifies the detections as NORMAL, SPLIT or SUFFERING FROM UPSTREAM TURBULENCE. The gaps are split and a suitable number of bands are inserted (Step 507).

The bands given the SPLIT classification are split a suitable number of times, with the division points being the centroid of the interval to be split. The centroid is used to place the insertion on the shoulder of a poorly defined band, and not in the bottom of the trough between the SPLIT band and its left neighbor. Depending upon the size interval, and the expected band spacing, one or more insertions may be made. Each insertion has a defined Begin, Middle and End scanline value.

Referring to FIG. 11 for more detail, each band pair considered by fuzzy logic block GapCheck has several attributes which are measured (Step 1101). In particular, the expected spacing curve, expected width curve, band width, left gap (gap to the leftmost neighbor) and sequence is determined. The upstream sequence is assigned a measure of GC-richness (Step 1102). These measurements, coupled with the GC richness of the sequence of the 5 bands to the left, are informative in identifying bands which need additional bands added to their left. The gap is normalized with respect to the expected spacing onto interval [−1 . . . inf] (Step 1103). Unlike the OmitOkN logic, where the logic determines if a band is located where it should be (independent of its absolute spacing but focusing instead on how far off the spacing curve it is), in the GapCheck logic block, the concern is on the absolute distance of the band from its left neighbor. If the gap is an integer multiple of the spacing curve (say three spaces from its left neighbor) two bands are inserted to its left to establish the proper spacing. In addition to the gap between bands in the pair, this logic also considers the widths of the bands. Band width is normalized onto interval [−1 . . . inf] (Step 1104). Usually, when band resolution decreases and a region in the observed trace contains fewer peaks than are required, one or both bands in the pair is wider than it should be. The gap between the bands can be marginal and the band width can be the determining factor. Finally, large gaps and band widths should be viewed less aggressively in the presence of upstream GC-richness.

Figure 12:
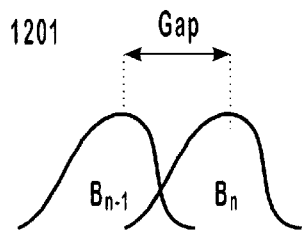
FIGS. 12 and 12B graphically illustrate the subject matter of the flowchart of FIG. 12A.
Figure 12A:
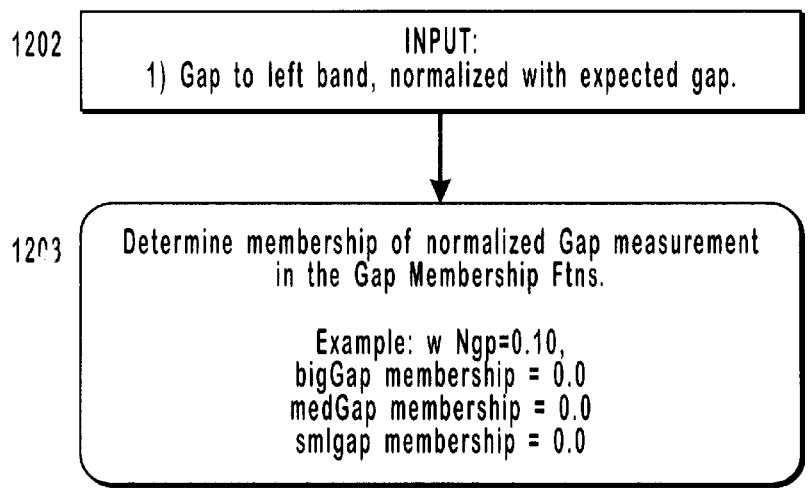
FIG. 12A depicts a flow chart of the GapCheck Gap Membership fuzzy logic block of FIG. 11.
Figure 12B:
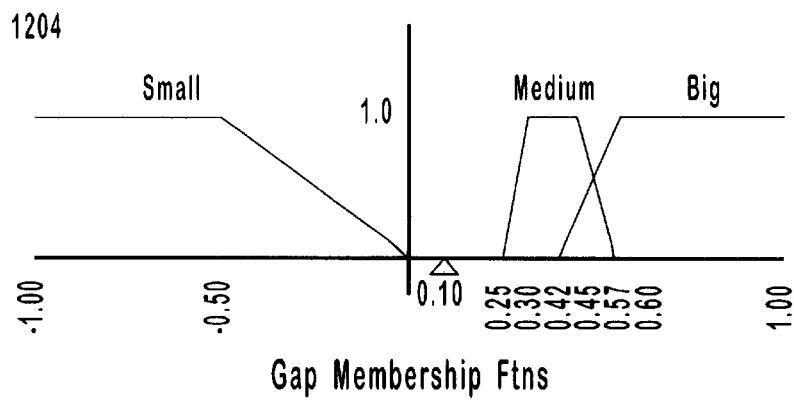

The normalized left-gaps of each band in a band pair are classified as big (Step 1105), medium (Step 1106) or small (Step 1107). FIG. 12 provides details of the GapCheck band gap membership function. Briefly, the membership function characterizes an observed gap measurement (ogp) if it differs from expectation (egp). The gap is measured between $B_n$ and $B_{n-1}$ (Step 1201). The observed gap is normalized to interval [−1 . . . inf] with the equation: ngp=ogp/egp−1.0. Referring to the example in Step 1203, a normalized gap of 0.1 is found to have 0.0 membership in all sets; that is, the gap meets expectations and is neither small, medium nor big (Step 1203).

Figure 13:
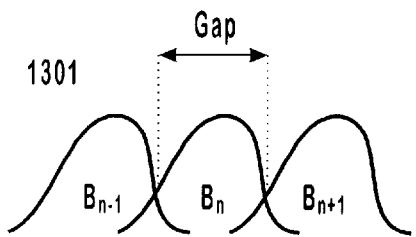
FIGS. 13 and 13B graphically illustrate the subject matter of the flowchart of FIG. 13A.
Figure 13A:
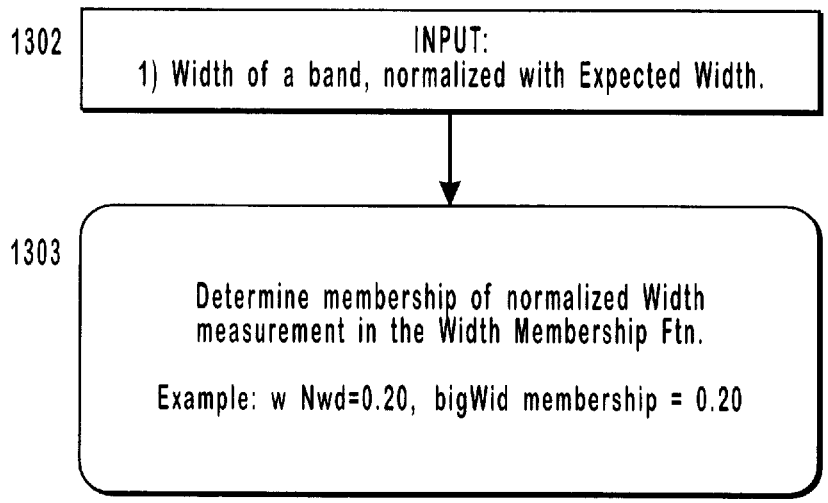
FIG. 13A depicts a flow chart of the GapCheck Width Membership fuzzy logic block of FIG. 11.
Figure 13B:
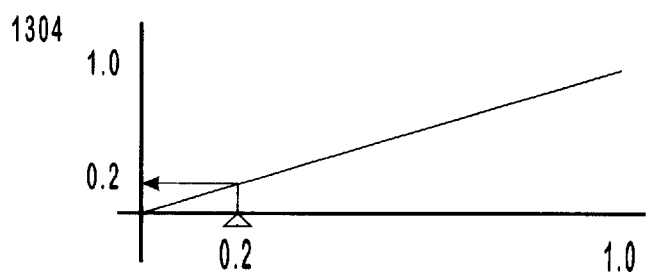

Referring to FIG. 11, in Step 1108 the normalized widths of each band in a band pair are classified as big. FIG. 13 provides details of the GapCheck band width membership function. This membership function characterizes an observed band width measurement (owd) if it exceeds expectations (ewd). The width is measured between $B_n$'s Begin and End points (Step 1301). In the example given in Step 1303, a normalized gap of 0.2 is found to have membership in BigWidth of 0.2; the band is not that wide, but it is wider than expected (Step 1304).

Referring to FIG. 11, in RULE NORM (Step 1109), $band_n$ is not marked as needing its left gap split if any of the following are TRUE:
  a) there is a large gap ($bigGap_n$) but the upstream sequence is GC-rich, or
  b) the gap to the first band in the pair is small ($smlGap_{n-1}$) and the two bands are not wide (!$bigWid_n$ and !$bigWid_{n-1}$) (i.e., ignore the gap between the bands), or c) the gap between the two bands is not large (!bigGap$_n$).

In step 1110, RULE SPLIT marks band$_n$ as needing its left gap split if either of the following are TRUE:
   a) the gap between the two bands is large (bigGap$_n$) and the first and/or second band is wide (bigWid$_{n-1}$ or bigWid$_n$) or,
   b) the gap between the two bands is large (bigGap$_n$) and the gap left of the first band is not small (!smlGap$_{n-1}$) and the upstream sequence is not gc-rich (!gcrich).

RULE SPLIT (a) detects the combination of a wide and normal band (in either order) while RULE SPLIT (b) selects a run of wide bands separated by large gaps. The strength of the rule firings is then used to scale the output sets (Step 1111). In example 1112, the output set NORMAL is scaled with amplitude 1.0 and output set SPLIT is scaled with 0.25. The conclusion is formed by calculating the centroid of the resultant "masses". In example 1112, the conclusion reached is that the band is NORMAL.

To identify putative peak insertion errors, Step 507 remeasures the cross banding, instantaneous spacing, band height, band amplitude, and the spacing (left and right gaps) to adjacent bands. The observed band spacing measurements are fit with a quadratic curve. This quadratic fit is used as the expectation of band spacing along the entire read segment. The OmitOkN Fuzzy logic block (Step 508) is then used to identify bands which are most likely insertion artifacts of the band detection process. Any and all such bands are removed from the putative peak set. Newly proposed insertions may be deleted in this step. The fuzzy logic band refinement stage adds the important advantage of reducing insertions and deletions and preventing arbitrary band calling when the reader encounters two or three base regions of signal dropout. See FIG. 6 and the accompanying text for details of insertion detection. The set of putative peaks which survive this processing are recorded as the bands for the read segment under consideration (Step 509).

C. Processing and Alignment

Referring to FIG. 1, reading function 104–106 consecutively processes sample segments until all of the input data set 101 is analyzed. Because each sample segment 104 overlaps the previous sample segment by a predetermined amount, the relative positioning of each read and aligned sample segment 106 is known. Step 107 assembles all of the read and aligned sample segments 106 to form a processed and reassembled sample segment 107.

D. Post-Processing Editing

In the working embodiment of the invention, a final process analyzes the set of measured band features with a third fuzzy logic block, BaseQual fuzzy logic block 109. This block assigns a quality measure to each called band. This block evaluates each band based on the band height, width, shape, left and right gap, cross-banding and baseline "buzz." This quality value, on the interval (0.0 to 1.0) can be used during subsequent sequence alignment/merging steps. The present invention uses the quality value to select the longest block of high quality sequence to be considered for alignment and merging with other sequences into a large DNA sequence. The algorithm that selects the left and right cutoff points generates a surface, with the x-axis labeled MOVING AVERAGE FILTER WIDTH, the y-axis labeled THRESHOLD, and the z-axis labeled READ LENGTH. The quality values are filtered with six moving average filters, and the filtered data is compared against nine thresholds. The longest contiguous block of above threshold filtered quality values provides the read length value for the surface for a particular filter width, threshold pair. Finally, this surface is scaled so that narrow filter and high threshold read lengths are favored over wide filter and low threshold read lengths. The surface maximum z-value is then chosen as the read length, and the associated first and last above threshold filtered quality value indexes serve as the left and right cutoff points, respectively. If a "preamble" sequence was submitted to this EDIT stage, and if the sequence is found beyond the established left cutoff point, the cutoff point is moved further left to exclude the "preamble" sequence.

Figure 15:
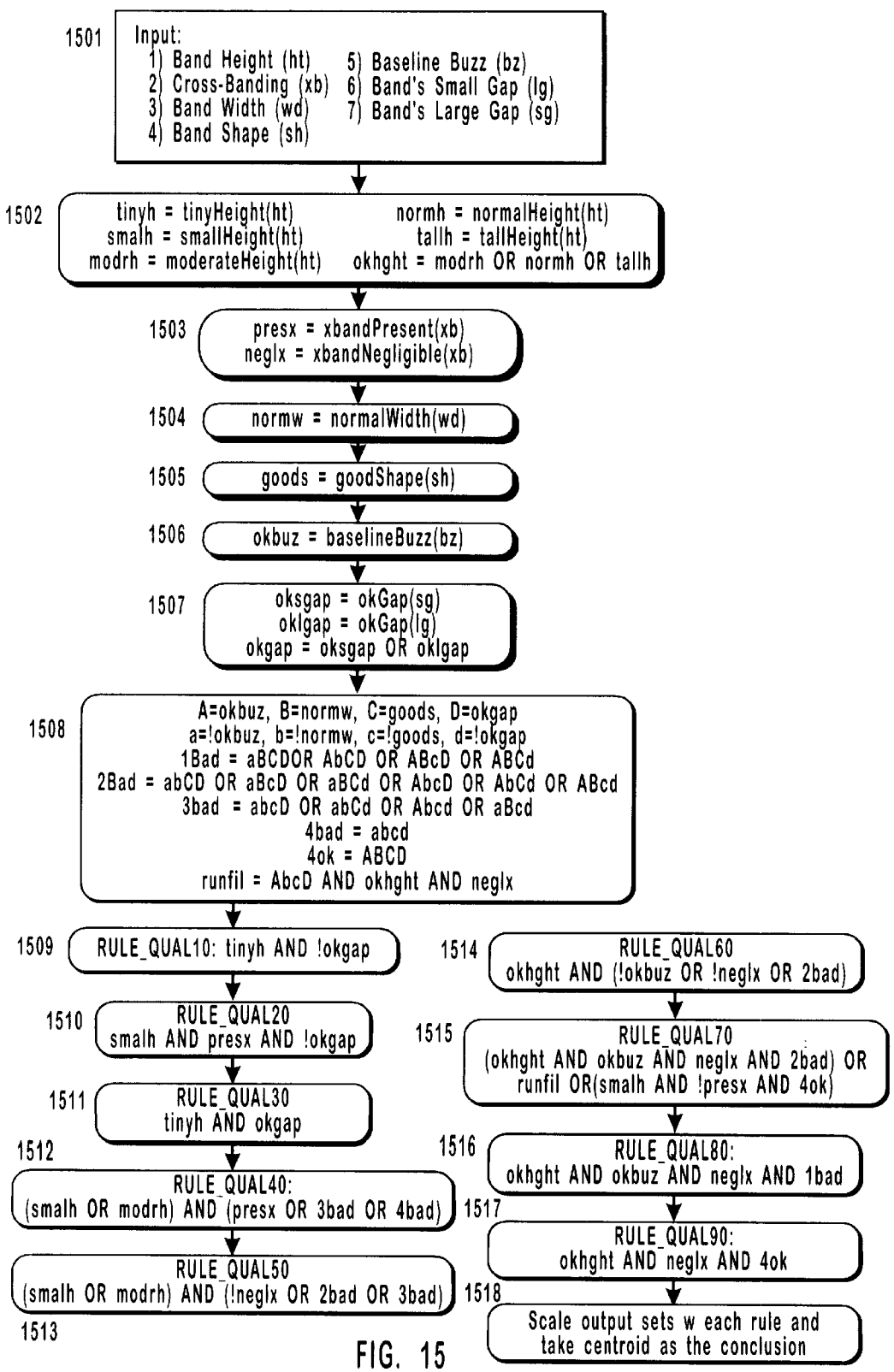
FIG. 15 depicts a flow chart of the BaseQual fuzzy
Figure 15A:
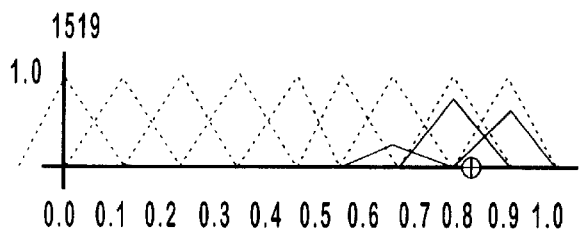
FIG. 15A graphically illustrates the subject matter of the flowchart of FIG. 15. logic block of FIG. 1.

Referring to FIG. 15, the BaseQual fuzzy logic algorithm assesses the quality of the called bases. Experience has shown that some sequence assembly algorithms fail to assemble sequences containing regions of incorrect sequence and that others can only succeed when each base is accompanied by an indication of its quality (or inversely, its probability of error). In the former case, if the incorrect sequence regions are masked from consideration by the assembly program, the bulk of the good sequence will successfully assemble. In the latter case, if the low quality regions are identified, the overall base caller product will assemble. In either case, incorrect sequence, encountered in isolation, can be and usually is identified by an experienced technician using visual inspection. That process is time consuming and monotonous and subtle errors may go undetected. In general though, incorrect base calling is done where the underlying data traces are marginal.

The BaseQual routine, automates quality assessment by measuring and analyzing multiple features (Step 1501) of each called base. Fuzzy logic is used to identify certain band presentation patterns and assign levels of quality to them. These band features include the band height, cross-banding, band width, band shape, the band's small gap and the band's large gap.

Figure 16:
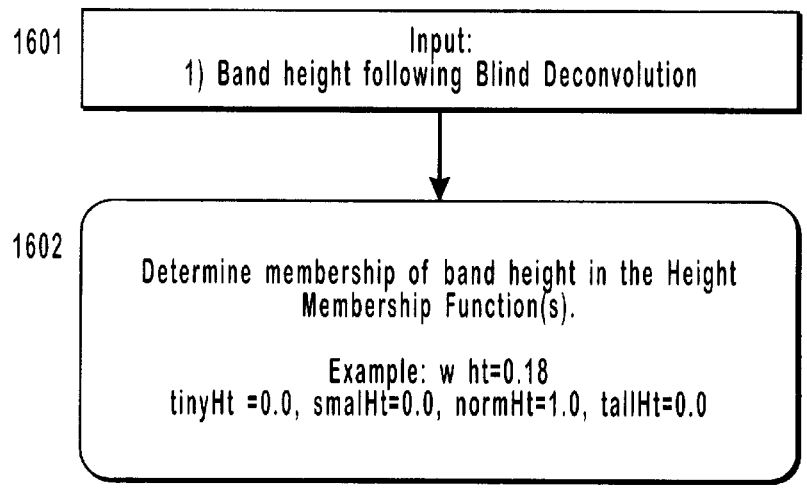
FIG. 16 depicts a flow chart of the BaseQual Height Membership fuzzy logic block of FIG. 15.
Figure 16A:
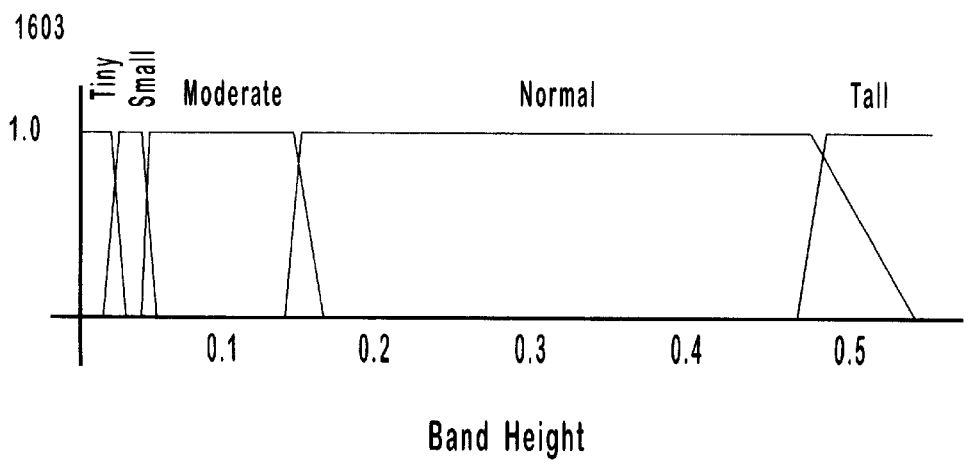
FIG. 16A graphically illustrates the subject matter of the flowchart of FIG. 16.

Band height variations are informative in many of the classifications. Six fuzzy variables are used to classify a band's height (tiny, small, moderate, normal, tall and collectively, OK) (Step 1502). Referring to FIG. 16 for details of the BaseQual height membership functions, the membership function characterizes an observed band height measurement. A band with a "tiny" or "small" height is usually suspect, with the tiny bands being more suspect that the merely small. Moderate height bands, and tall bands, also require scrutiny. Tall bands are suspect because usually they are found amid stops, compressions, and, on slab gels, artifacts. In the example given in Step 1602, a band height of 0.18 is found to have membership in NormalHeight of 1.0, which is to say that the band's height is within tolerances (See Example 1603).

Figure 17:
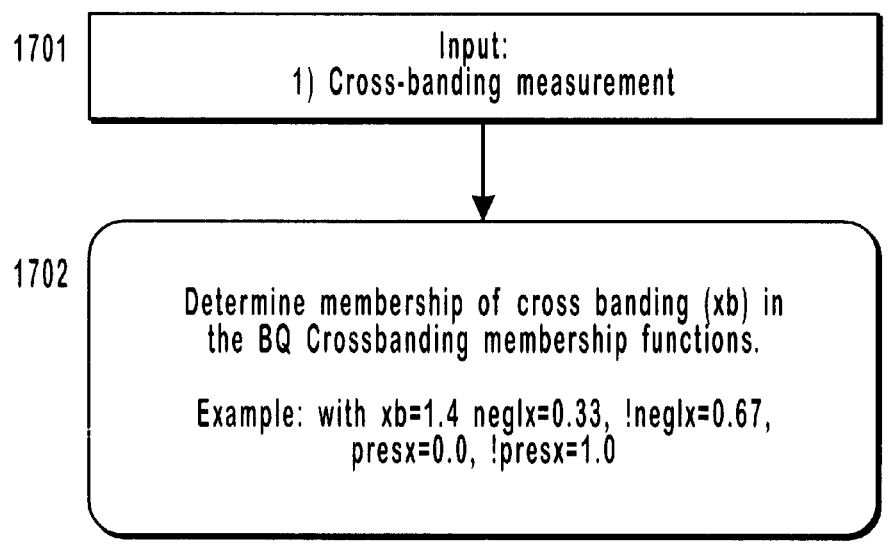
FIG. 17 depicts a flow chart of the BaseQual Cross Banding Membership fuzzy logic block of FIG. 15.
Figure 17A:
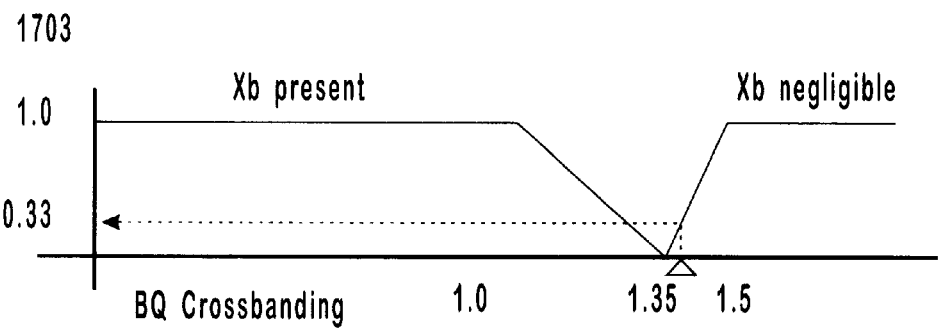
FIG. 17A graphically illustrates the subject matter of the flowchart of FIG. 17.
Figure 18:
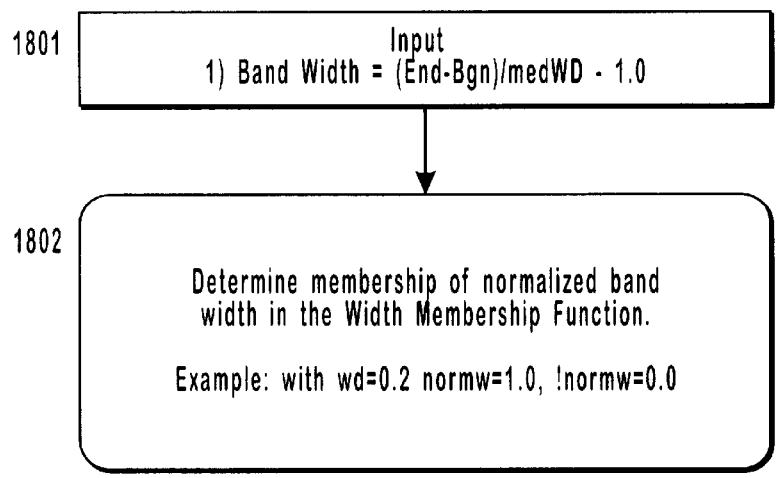
FIG. 18 depicts a flow chart of the BaseQual Width Membership fuzzy logic block of FIG. 15.
Figure 18A:
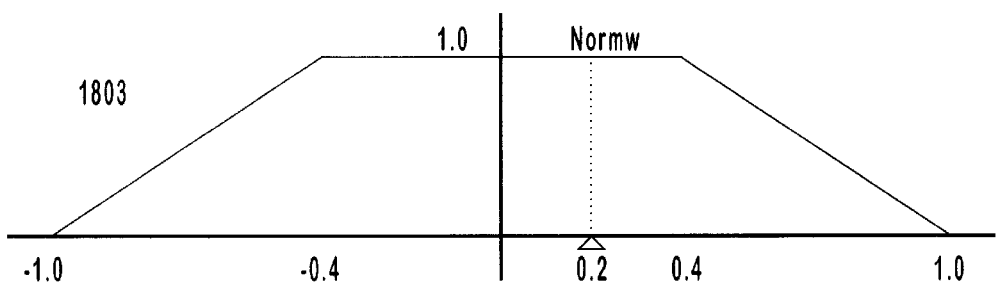
FIG. 18A graphically illustrates the subject matter of the flowchart of FIG. 18.
Figure 19:
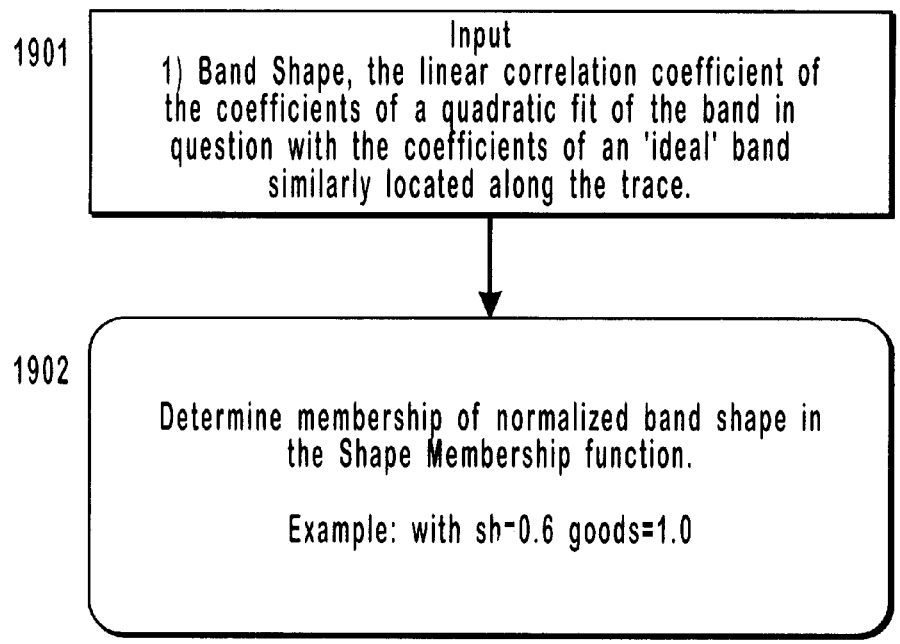
FIG. 19 depicts a flow chart of the BaseQual Shape Membership fuzzy logic block of FIG. 15.
Figure 19A:
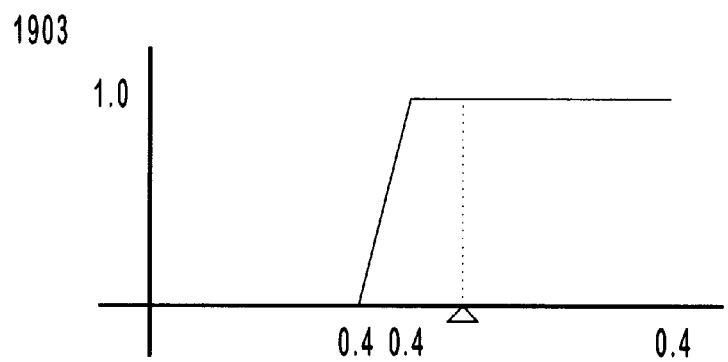
FIG. 19A graphically illustrates the subject matter of the flowchart of FIG. 19.

Referring to Step 1503, cross banding, the measure of competition by two traces for the same region of the trace, is also informative. Referring to FIG. 17, the BaseQual cross banding membership functions characterize an observed band's cross banding measurement. The cross banding measurement is the ratio of the dominant trace to the next dominant trace. Ratios above 1.5 are deemed to have negligible cross banding, whereas those with lower ratios (with 1.0 being the lowest ratio possible) are suspect. Referring to the example in FIG. 1702, a cross banding ratio of 1.35 is found to have membership in negligiblexb of 0.33 (and 0.67 in the negation, !negligibleXb). Referring to Step 1504, band width (normalized based on a quadratic fit of observed band widths), is another informative variable. In FIG. 18, the BaseQual band width membership function, a band's observed width is normalized with respect to the expected band width. The intent of the membership function is to determine how normal the normalized band width is. Referring to the example in Step 1802, a normalized width of 0.2 has membership in the Normal set of 1.0 (See Example 1803). Referring to Step 1505, the band shape, the linear correlation coefficient between the coefficients of a quadratic fit of the band and the coefficients of a quadratic fit of an ideal band, identifies abnormally shaped bands. The Base-Qual band shape membership function is informative in determining the quality of the base call. The range of band heights and widths observed in a run varies considerably. In one embodiment, sample rate conversion normalizes the observed band width, the band amplitude was normalized to 1.0, and the result was then compared against an ideal, gaussian bell-shaped band. The approach is computationally expensive and much information regarding the observed shape is discarded through the morphing process.

In a more preferred embodiment, each band's height values are fit with a quadratic curve. Similarly, an ideal band shape is fit with a quadratic curve. (The ideal band shape is defined to have normal height and the expected width.) This approach reduces each sample set to an equal number of points. The shape metric is taken as the linear correlation coefficient of these two sample sets. Experience has shown that a band's shape is "abnormal" if this shape metric falls below 0.5. Referring to the example in Step 1902, a shape metric of 0.6 is found to have membership in GoodShape of 1.0 (See example 1903).

Figure 20:
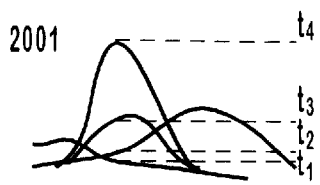
FIGS. 20 and 20B graphically illustrate the subject matter of the flowchart of FIG. 20A.
Figure 20A:
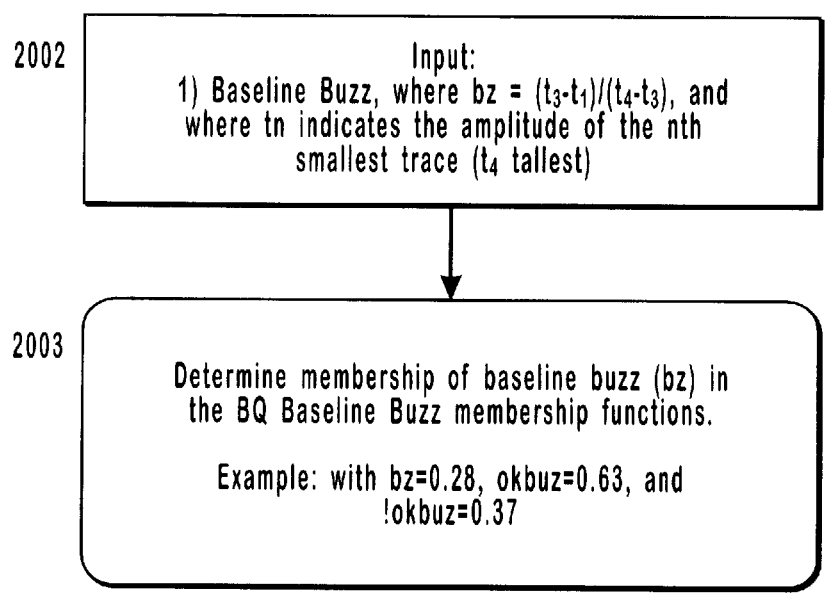
FIG. 20A depicts a flow chart of the BaseQual Baseline Buzz Membership fuzzy logic block of FIG. 15.
Figure 20B:
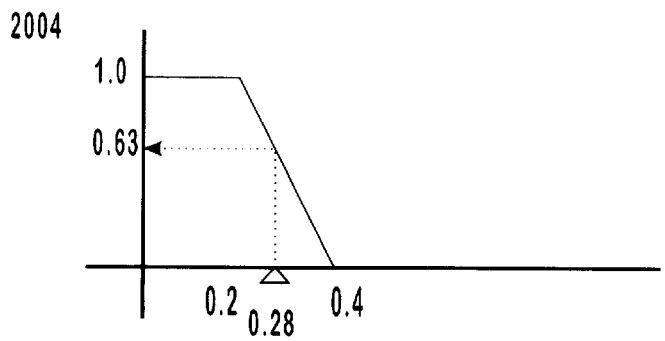

Referring to Step 1506, "baseline buzz," defined as the ratio of two other ratios, helps identify regions of the trace (usually the ends) where there is competition by several traces for the called band's domain. Toward the margins of a trace the baseline can often become quite busy, and when it does the quality of the underlying data, and the reads made thereon, become suspect. Baseline buzz can result from either incorrect signal processing, or from underlying data being so erratic as to defy correct signal processing. In either case the called sequence should come under suspicion. Referring to FIG. 20, a buzz measurement above 0.2 begins to signal a problematic sequence. Referring to the example is step 2003 and Example 2004, a buzz measurement of 0.28 has membership in okBuz of 0.63 (and 0.37 in the negation, !okBuz). In this case, the band's quality has come into question.

Figure 21:
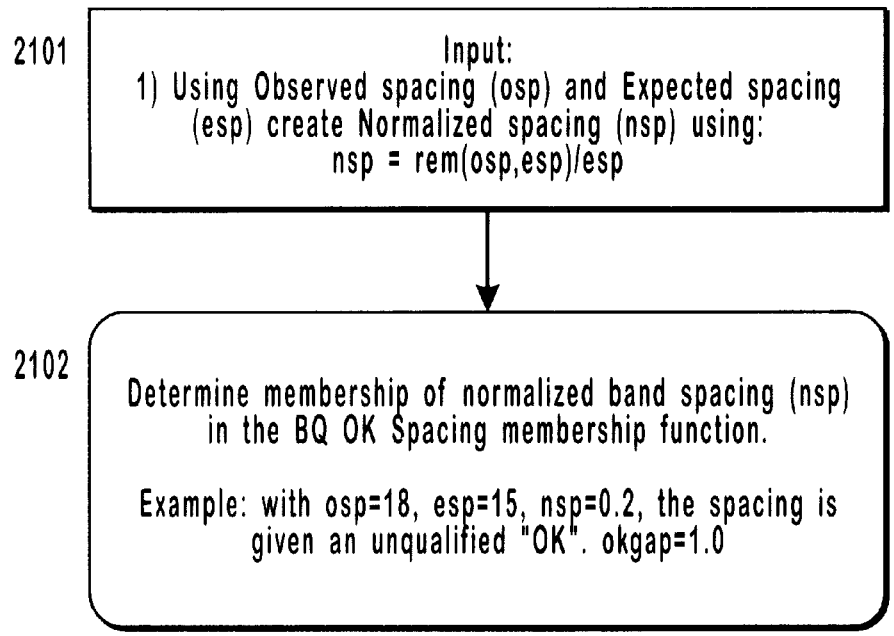
FIG. 21 depicts a flow chart of the BaseQual OK Spacing Membership fuzzy logic block of FIG. 15.
Figure 21A:
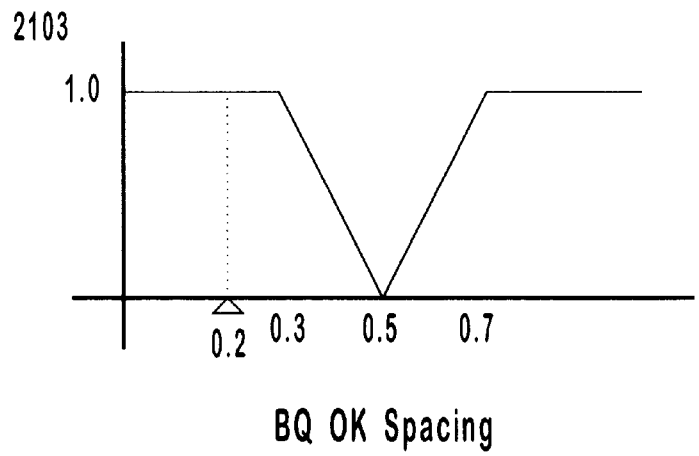
FIG. 21A graphically illustrates the subject matter of the flowchart of FIG. 21.

Referring to Step 1507, the gaps to a band's left and right neighbor are further informative variables in assessing band quality. These measurements help identify bands that, despite all previous efforts to the contrary, remain positioned too close or too far from a preferred position. Referring to FIG. 21 for details of BaseQual band spacing membership functions, a band's observed spacing is normalized with respect to the expected spacing. The intent of the membership function is to determine how normal the normalized band spacing is. In the example given in blocks 2102 and 2103, a normalized spacing of 0.2 receives an unqualified OK, with membership in OK Spacing of 1.0.

Referring to Step 1508, logical combinations of several variables (e.g. buzz, width, shape, and spacing) help keep the rules for assigning a quality value to a band tractable. Variable 1bad indicates that one of the measures was out of tolerance. Similarly, variables 2Bad, 3Bad, and 4Bad indicate that two, three, or all four measurements are out of tolerance. Finally, variable 4Ok notes that all four measurements are in tolerance.

Subsequently, a quality assessment is determined through application of a series of nine rules. In RULE QUAL10, the lowest quality assessment is made of bands that are tiny in height and are incorrectly positioned (Step 1509). For a band which matches this rule to some degree, the rule will assign a nonzero scale value to the output set with centroid near 0 (Step 1519). The second quality assessment, RULE QUAL20, is made of bands that are short, show signs of cross banding, and are incorrectly positioned (Step 1510). For a band which matches this rule to some degree, the rule will assign a nonzero scale value to the output set with centroid near 13 (Step 1519).

The third quality assessment, RULE QUAL30, is made of bands which are tiny in height yet correctly positioned (Step 1511). A band which matches this rule to some degree will be assigned a nonzero scale value to the output set with centroid near 25 (Step 1519). The fourth quality assessment, RULE QUAL40, is made of bands with small or moderate height and which show signs of cross banding or have 3Bad or 4Bad attributes (Step 1512). A band which matches this rule to some degree will be assigned a nonzero scale value to the output set with centroid near 38 (Step 1519).

The fifth quality assessment, RULE QUAL50, is made of bands with small or moderate height and which show either some degree of cross banding or have 2Bad or 3Bad attributes (slightly better than quality class 4 in that these might have one less bad attribute) (Step 1513). A band which matches this rule to some degree will assign a nonzero scale value to the output set with centroid near 50 (Step 1519). RULE QUAL60, the sixth quality assessment, is applied to bands with OK height but which show signs of baseline buzz, non-negligible cross banding, or have 2Bad attributes (Step 1514). A band which matches this rule to some degree will assign a nonzero scale value to the output set with centroid near 63 (1519).

Bands which have higher degrees of quality satisfy the seventh to ninth quality assessments. The seventh quality assessment, RULE QUAL70, is made of bands in one of three general classes. (Step 1515). One class of bands has OK height, little baseline buzz, negligible cross banding, but has 2Bad attributes. Another class of bands shows negligible cross banding, has OK height, no baseline buzz, is correctly positioned, but has both abnormal width and bad shape. (This class, named runfil, is characteristic of a band inserted within a poorly resolved run of bands). The final class of bands has 4Ok attributes but has small height and possibly some degree of cross banding present. A band which matches this rule to some degree will assign a nonzero scale value to the output set with centroid near 75. (Step 1519).

The eighth quality assessment, RULE QUAL80, is made of bands with OK height, little baseline buzz, negligible cross banding, but 1Bad attribute. (Step 1516). A band which matches this rule to some degree (many do) will assign a nonzero scale value to the output set with centroid near 88. (Example 1519). The top quality assessment, RULE QUAL90, is made of bands with absolutely nothing visually wrong with them (Step 1517). A band which matches this rule to some degree (again, given good quality input, many do) will assign a nonzero scale value to the output set with centroid near 100 (1519). Finally, as with all the other fuzzy logic blocks, the output sets are scaled with the strength of their respective rule firings, and the centroid is calculated to determine the final quality assessment.

E. Final Sequence Assembly

The final quality assessments from the BaseQual Fuzzy Logic analysis control the length of the final sequence 109. Where high quality sequence data is desired, the quality assessments determines may limit the read length of the final sequence. Where longer read lengths are desired, and lower quality sequence is acceptable, the quality assessments can aid is correlating the resulting sequence data from other sequence analysis. For example, when overlapping sequences are obtained, the quality assessments can determine which base calls are more reliable. Similarly, when both strands of a DNA sequence are available, the quality assessments aid in identifying higher probability base calls.

F. Computer Implementation of the Base Calling Software

The invented Base Calling Software can be implemented on standard desktop computers, such as Pentium- and 486-containing PC's. Computers with less powerful processors are also suitable, although the overall processing time for each input data set will be slower. Such computers will preferably include at least a central processing unit, dynamic memory and a device for outputting processed information. The invented base calling software can be stored on any suitable storage media, including computer diskettes, removable media, hard-drives, CD's, magnetic tapes and similar electronic storage means.

While the present invention has been described and illustrated in conjunction with a number of specific embodiments, those skilled in the art will appreciate that variations and modifications may be made without departing from the principles of the invention as herein illustrated and described.

The invention may be embodied in other specific forms without departing from the spirit or essential characteristics thereof. The present embodiments are to be considered in all respects as illustrative, and not restrictive.

What is claimed is:

1. A computer-implemented method for determining base identity in unprocessed nucleic acid sequencing data, comprising the steps of:

receiving unprocessed input data comprising unprocessed nucleic acid sequencing data;

preprocessing said input data to generate preprocessed data;

blind deconvolving said preprocessed data to generate blind deconvolved data;

extranormalizing said blind deconvolved data to generate extranormalized data;

detecting peaks in said extranormalized data using peak detection means to generate processed data;

editing the quality of said processed data using fuzzy logic editing means to generate called nucleotide sequence and at least one quality value for said called sequence.

2. The method according to claim 1, wherein said preprocessing step comprises:

identifying Begin and End points in said unprocessed data;

establishing a baseline in said unprocessed data;

subtracting said baseline from said unprocessed data to generate baseline-subtracted data; and separating said baseline-subtracted data to generate preprocessed data, said separating step comprising spectral or leakage separation.

3. The method according to claim 1, wherein said extranormalizing step further comprises:

correcting the relatives mobility of signals in said blind deconvolved data using Monte Carlo alignment means.

4. The method according to claim 3, wherein said extranormalizing step further comprises:

attenuating signals which were accentuated by said blind deconvolving.

5. The method according to claim 1, wherein said peak detection means comprises:

fuzzy logic insertion detection means to identify and remove putative insertions in said extranormalized data; and fuzzy logic gapchecking means to identify putative gaps in said extranormalized data and inserting data in said gaps.

6. The method according to claim 5, further comprising:

analyzing said extranormalized data with said fuzzy logic insertion detection means before and after analyzing said extranormalized data with said fuzzy logic gap checking means.

7. The method according to claim 1, wherein said editing means generates at least one quality value by analyzing characteristics of said processed data selected from the group consisting of band height, band width, band shape, band's left gap, band's right gap, cross-banding and baseline buzz.

8. The method according to claim 7, wherein said editing means generates at least one quality value from said characteristics of said processed data by applying a plurality of fuzzy logic rules.

9. The method of claim 1, wherein said blind deconvolving is iterative and includes at least a first narrow-band guess for the filter band width value and a refined second band width for the filter band width value.

10. A computer-implemented method for identifying DNA sequence in unprocessed nucleic acid sequencing data, comprising the steps of:

receiving unprocessed input data comprising unprocessed nucleic acid sequencing data;

preprocessing said input data to generate preprocessed data;

blind deconvolving said preprocessed data to generate blind deconvolved data;

extranorrnalizing said blind deconvolved data to generate extranormalized data;

detecting peaks in said extranormalized data to generate peak detected-data;

identifying and removing insertions in said peak detected-data using a fuzzy logic insertion detection algorithm;

identifying and filling gaps in said peak detected-data using a fuzzy logic gap checking algorithm; and producing processed sequence data.

11. The method of claim 10, further comprising:

editing the quality of said processed sequence data using fuzzy logic editing means to generate called nucleotide sequence and at least one quality value for said called sequence.

12. The method according to claim 10, wherein said preprocessing step further comprises:

identifying Begin and End points in said unprocessed data;

establishing a baseline in said unprocessed data;

subtracting said baseline from said unprocessed data to generate baseline-subtracted data;

separating said baseline-subtracted data to generate preprocessed data, said separating step comprising spectral or leakage separation.

13. The method according to claim 10, wherein said extranormalizing step further comprises:

correcting the relatives mobility of signals in said blind deconvolved data using a Monte Carlo alignment.

14. The method according to claim 13, wherein said extranormalizing step further comprises:

attenuating signals accentuated by blind deconvolving.

15. The method according to claim 10, further comprising:

analyzing said extranormalized data with said fuzzy logic insertion detection algorithm before and after analyzing said extranormalized data with said fuzzy logic gap checking algorithm.

16. The method according to claim 11, wherein said editing means generates at least one quality value by analyzing characteristics of said processed data selected from the group consisting of band height, band width, band shape, band's left gap, band's right gap, cross-banding and baseline buzz.

17. The method according to claim 16, wherein said editing means generates at least one quality value from said characteristics of said processed data by applying a plurality of fuzzy logic rules.

18. The method of claim 10,
wherein said blind deconvolving is iterative and includes at least a first narrow-band guess for the filter band width value and a refined, second guess for the filter band width value.

19. A computer-implemented method of determining a nucleotide sequence of a DNA molecule comprising:
providing a set of lane signals encoding the migration pattern of a DNA molecule subjected to DNA sequence analysis to generate an input data;
preprocessing said input data to generate preprocessed data, said preprocessing comprising at least one of the following steps:
identifying Begin and End points,
subtracting baseline noise,
spectrally separating said input data using a separation matrix to correct for spectral cross-talk, and
leakage separating said input data using a separation matrix to correct for lane leakage;
blind deconvolving said preprocessed data to generate blind deconvolved data, said blind deconvolving deblurring signals in said preprocessed data and normalizing signal amplitudes, said blind deconvolving using an iterative filter band width algorithm;
extranormalizing said blind deconvolved data to generate extranormalized data, said extranormalizing including at least one of the following steps:
correcting relative signal mobility differences using a Monte Carlo alignment, and
attenuating signals accentuated by blind deconvolution;
detecting peaks in said extranormalized data to generate peak detected-data;
identifying and removing insertions in said peak-detected data using a fuzzy logic insertion detection algorithm;
identifying and filling gaps in said peak-detected data using a fuzzy logic gap checking algorithm; and
producing processed sequence data.

* * * * *